US011890135B2

(12) United States Patent
Datta et al.

(10) Patent No.: US 11,890,135 B2
(45) Date of Patent: Feb. 6, 2024

(54) INTEGRATED IMAGING AND DEVICE DEPLOYMENT PLATFORM

(71) Applicant: Evalve, Inc., Santa Clara, CA (US)

(72) Inventors: Saurabh Datta, Pleasanton, CA (US); Chad J. Abunassar, Alameda, CA (US)

(73) Assignee: EVALVE, INC., Santa Clara, CA (US)

( * ) Notice: Subject to any disclaimer, the term of this patent is extended or adjusted under 35 U.S.C. 154(b) by 16 days.

(21) Appl. No.: 17/363,670

(22) Filed: Jun. 30, 2021

(65) Prior Publication Data
US 2022/0000445 A1 Jan. 6, 2022

Related U.S. Application Data

(60) Provisional application No. 63/047,382, filed on Jul. 2, 2020.

(51) Int. Cl.
| | |
|---|---|
| *A61B 8/00* | (2006.01) |
| *A61B 8/12* | (2006.01) |
| *A61B 8/08* | (2006.01) |
| *A61M 25/01* | (2006.01) |

(52) U.S. Cl.
CPC .......... *A61B 8/0841* (2013.01); *A61B 8/0883* (2013.01); *A61B 8/12* (2013.01); *A61B 8/4254* (2013.01); *A61B 8/445* (2013.01); *A61B 8/4416* (2013.01); *A61B 8/466* (2013.01); *A61M 25/0147* (2013.01)

(58) Field of Classification Search
CPC ....... A61B 8/0841; A61B 8/0883; A61B 8/12; A61B 8/4254; A61B 8/4416; A61B 8/445; A61B 8/466
See application file for complete search history.

(56) References Cited

U.S. PATENT DOCUMENTS

| | | | |
|---|---|---|---|
| 2009/0088631 A1* | 4/2009 | Dietz | A61B 90/37 600/424 |
| 2012/0165680 A1* | 6/2012 | Akifumi | A61M 25/0662 600/466 |
| 2013/0223702 A1 | 8/2013 | Holsing et al. | |
| 2017/0086974 A1* | 3/2017 | Lashinski | A61B 8/0883 |
| 2018/0055347 A1* | 3/2018 | Teixeira Dos Santos Paulo | A61B 8/52 |
| 2019/0060003 A1* | 2/2019 | Tuason | A61B 34/20 |
| 2019/0142589 A1* | 5/2019 | Basude | A61F 2/2463 623/2.11 |
| 2019/0167197 A1* | 6/2019 | Abunassar | A61F 2/246 |
| 2019/0274658 A1* | 9/2019 | Stigall | A61B 8/445 |
| 2021/0393334 A1* | 12/2021 | Wilson | A61M 25/0136 |
| 2022/0265280 A1* | 8/2022 | Chamorro | A61M 25/0136 |

* cited by examiner

*Primary Examiner* — Boniface N Nganga
*Assistant Examiner* — Zainab Mohammed Aldarraji
(74) *Attorney, Agent, or Firm* — Workman Nydegger

(57) ABSTRACT

An integrated imaging and device deployment platform and method may include a catheter, at least one imaging unit, at least one deployment unit, and at least one device configured to be deployed by the at least one deployment unit. The integrated imaging and device deployment platform facilitates improved navigation and deployment of a therapeutic or medical device by providing the at least one imaging unit proximate the deployment unit. Information generated from the at least one imaging unit may be utilized with additional imaging modalities to provide improved imaging and delivery of devices while reducing use of X-ray radiation and contrast injection.

20 Claims, 12 Drawing Sheets

INTEGRATED IMAGING AND DEVICE DEPLOYMENT PLATFORM

CROSS-REFERENCE TO RELATED APPLICATIONS

This application claims the benefit of and priority to U.S. Provisional Application No. 63/047,382, filed on Jul. 2, 2020, entitled "INTEGRATED IMAGING AND DEVICE DEPLOYMENT PLATFORM," the entire contents of which are hereby incorporated by reference.

BACKGROUND OF THE INVENTION

Precise visualization and navigation of minimally invasive therapeutic devices during a procedure are essential to ensure successful deployment of the minimally invasive device. Therapeutic devices such as catheters, stents, clips, and other devices used in treatments of various pathologies are often deployed using imaging guidance by a combination of ultrasound and X-ray based imaging modalities.

Fluoroscopic imaging, comprising an X-ray source and a fluorescent screen, combined with contrast injection is often needed to identify a device position relative to a patient's anatomy. However, use of fluoroscopic imaging with contrast injection may be contraindicated for patients with renal disease, diabetes, hypertension, heart failure, multiple myeloma, advanced age, use of other nephrotoxic drugs, or dehydration. Contrast dyes may elicit an allergic reaction, for example, or may result in contrast nephropathy. Radiation has the inherent disadvantage of being carcinogenic.

In procedures such as left atrial appendage occlusion ("LAA") occlusion procedure, the use of ultrasound imaging, including both transesophageal echocardiography ("TEE") and intra-cardiac echocardiography ("ICE") imaging, have been shown to reduce the need for fluoroscopy and the attendant patient-health risks while simultaneously improving patient outcomes.

Cardiac ablation procedures additionally rely on a three-dimensional visualization platform that can create a map of 3D anatomy and merge information based on pre-acquired computed tomography ("CT") imaging for an accurate representation of a patient's anatomical details. The patient's anatomy is mapped by moving a mapping catheter inside the heart chamber of interest and generating an accurate 3D model of the heart. This may require the use of a suitable non-fluoroscopic 3D cardiac mapping and catheter navigation system modality such as the Ensite™ Cardiac Mapping System available from Abbott Laboratories of Chicago, IL, and suitable for mapping cardiac features and conditions.

The location of the device catheter can be located during such a procedure can be determined using a magnetic- or impedance-based sensor and can be visualized in the 3D anatomical model in real-time. This method is used in catheter-based ablation methods. Providing an imaging device that is capable of carrying out simultaneous imaging may provide further anatomical, functional, hemodynamic, navigational, or procedural information during certain steps of a surgical or minimally invasive procedure.

While attempts have been made to provide imaging solutions that mitigate the risks of fluoroscopy and contrast injection, and to improve a user or practitioner's ability to navigate a patient's anatomy during a medical procedure, existing imaging solutions do not provide an imaging solution that synergistically combines multiple imaging modalities to yield an improved real-time image or rendering of the patient's anatomy for use during a procedure and that avoids the radiation exposure and risks from contrast injection attendant to existing solutions.

There is a need for an integrated imaging and device deployment platform and method for using same that provides a combination of 3D mapping with a catheter, positional information from a sensor, and imaging information from a catheter-based system, such that the platform can provide complementary information to enable and facilitate minimally invasive procedures that are safe and do not require dangerous levels of radiation-based imaging. There is a need for providing such information simultaneously and in real-time so as to assist in guiding a minimally invasive procedure to improve the ease of the procedure and patient outcomes.

BRIEF SUMMARY OF THE INVENTION

Embodiments of an integrated imaging and device deployment platform and method for using the same according to the disclosure address the problem of imaging and delivery or deployment systems being poorly suited to providing and utilizing complementary imaging modalities and being limited in scope and prone to harming patients through fluoroscopy. The disclosed embodiments advantageously provide an integrated imaging and deployment platform that allows a user to map and navigate a patient's anatomy during a procedure.

In embodiments, the integrated imaging and device deployment platform may comprise an imaging device, such as an intracardiac imaging device. An intracardiac imaging device may include an ultrasound catheter or any other suitable modality. The platform may further comprise a catheter-based device for deployment. A device for deployment from the disclosed embodiments may include a device suitable for minimally invasive operations and therapies, such as a MitraClip® fixation device available from Abbott Vascular of Santa Clara, CA, USA. In other embodiments, the device may be a left atrial appendage ("LAA") occlusion device. Other devices may be used as suitable. The device may be steerable to facilitate ease of guidance, navigation, and articulation, both for imaging and for deployment of the device.

The platform and method may utilize detailed anatomical information obtained from a computed tomography (CT) image, model, or rendering acquired before an operation. Alternatively or in addition, the platform and method may utilize a 3D rendering generated from a mapping catheter.

The platform and method may be configured to receive and utilize real-time information regarding the position of the device from one or more embedded sensors in the device. The real-time information may be tracked in a 3D space corresponding to the patient's anatomy, such as the patient's heart, whereby anatomical details may be visualized with a component or independent imaging catheter. The independent imaging catheter in embodiments is an intracardiac echocardiography (ICE) catheter. The one or more sensors may be embedded in the imaging catheter or may be provided in an accessory catheter. Information from the embedded sensors may be used to determine a position of the imaging or accessory catheter relative to the device and/or the anatomy of the user.

By utilizing the information obtained from the embedded sensors, the imaging catheter can be better positioned by a user or practitioner to a desired position so as to guide the deployment of the device or tissue interaction. For example, if the device is a MitraClip® or other edge-to-edge leaflet approximation device, the embedded sensors may be used to guide the imaging catheter to better facilitate leaflet grasping. Additionally, positioning of the imaging catheter or other imaging device as well as the device (e.g. a minimally invasive therapy device) relative to the anatomy of the patient is important in LAA occlusion procedures.

The information provided from each component or associated system of the integrated platform, including the imaging device, the pre-acquired CT image or 3D rendering from the mapping catheter, and/or the embedded-sensor information, may be utilized by the platform to enable navigation and deployment of the device during a procedure. In embodiments, at least two such information modalities may be utilized in combination by the platform. In embodiments, all three such information modalities may be utilized in combination.

By providing a plurality of imaging modalities in the integrated imaging and device deployment platform and method according to the disclosed embodiments, a user may properly position a device and deployment modality such as a catheter relative to a particular anatomical feature of a patient while minimizing the amount of radiation and contrast dye that is required, thereby minimizing risk and harm to the patient without compromising the user's ability to accurately utilize or deploy the device.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which.

Figure 1:
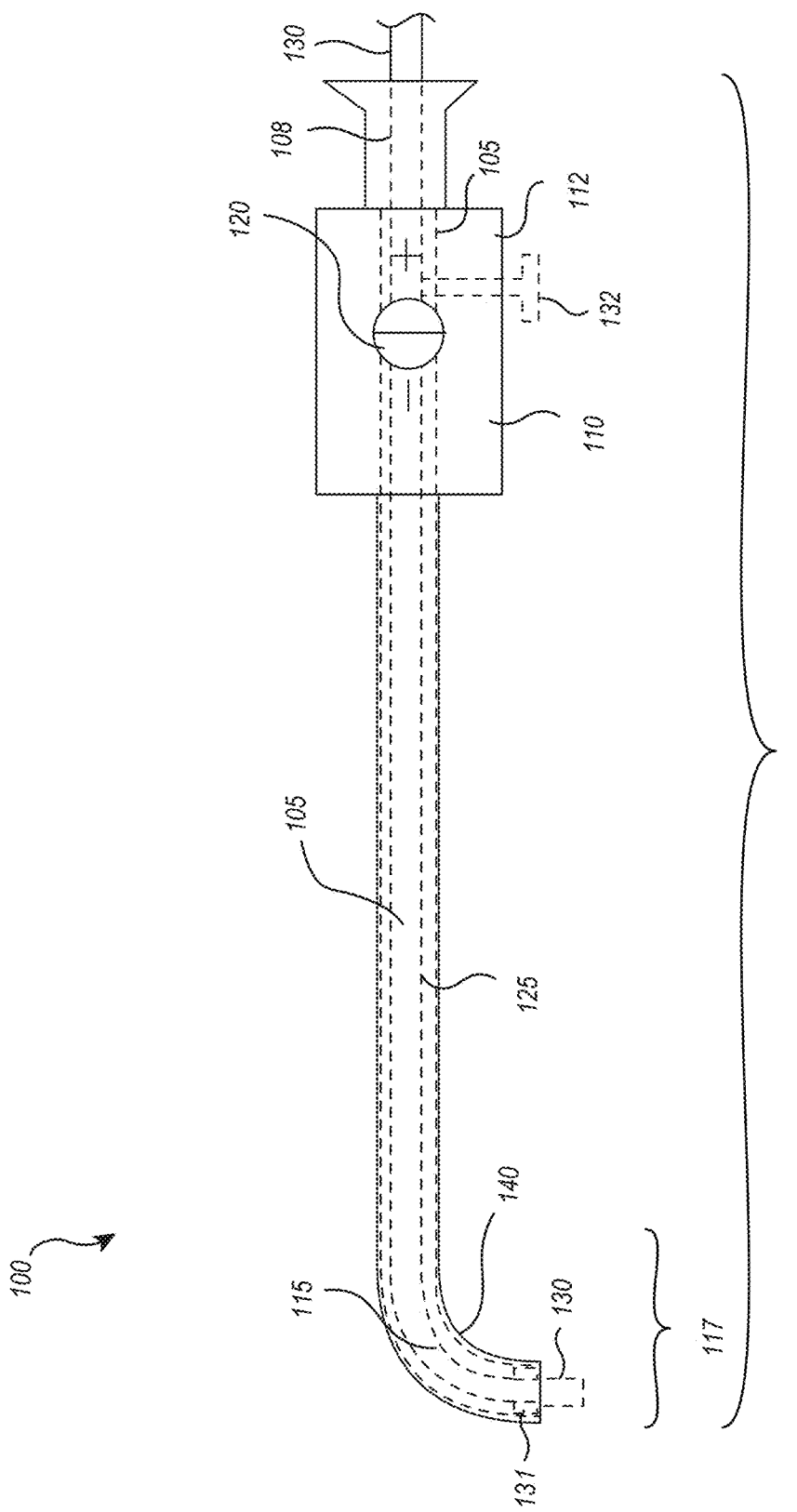
FIG. 1 illustrates in elevational view an integrated imaging and device deployment platform according to an embodiment.

The drawing figures are not necessarily drawn to scale, but instead are drawn to provide a better understanding of the components, and are not intended to be limiting in scope, but to provide exemplary illustrations. The figures illustrate exemplary embodiments of methods, systems, and devices for deploying an implant, and in no way limit the structures, configurations, or functions of embodiments according to the present disclosure.

DETAILED DESCRIPTION OF THE PREFERRED EMBODIMENTS

I. General Overview

The present invention provides an integrated imaging and device deployment platform and method for improving patient outcomes in medical procedures, such as minimally invasive procedures, while minimizing radiation exposure and other risks to the patient. The integrated imaging and device deployment platform and method of the disclosed embodiments may synergistically combine one or more imaging modalities in an integrated imaging and device deployment platform that improves a practitioner or user's ability to accurately image, navigate, and/or treat a patient's anatomy while reducing risk factors associated with existing imaging and delivery modalities.

FIG. 1 illustrates an embodiment of a delivery system 100 of, for example, an integrated imaging and device deployment platform, that may be utilized for guiding and/or delivering a device. The device may be a MitraClip® mitral fixation device or an LAA occluder device. The desired region may be an anatomical location such as a cardiac valve.

In at least one embodiment, the delivery system 100 includes a deployment system 102 that may be utilized for guiding and/or delivering a device 130 to the anatomical location. The deployment system 102 can include a guide catheter 105 having a proximal end 112 and a distal end 115. The deployment system 102 may comprise a handle 110 positioned on or proximate the proximal end 112 of the guide catheter 105.

The guide catheter 105 may be operatively coupled to the handle 110. The guide catheter 105 may include a steerable portion 117 near the distal end 115 that can be steerable or maneuverable to enable the guiding and orienting of the guide catheter 105 through a body lumen, such as the patient's vasculature, to a targeted treatment site or anatomical location, such as a mitral valve and the tricuspid valve. Additionally, the guide catheter 105, and more generally the operational principles and structures associated therewith, can be used with other valve repair devices, such as valve fixation (leaflet grasping) devices, annuloplasty valve repair devices, and other valve repair devices. Further, as illustrated, the handle 110 may include at least one control 120 (e.g., a dial, a switch, a slider, a button, etc.) that can be actuated to control the movement and curvature of a steerable portion 117 of the guide catheter 105. In embodiments, the steerable portion 117 and the guide catheter 105 may be translatable axially, rotatable, bendable in one or more locations and/or directions, combinations thereof, and otherwise maneuvered or steered.

In at least one embodiment, the at least one control 120 can be operatively coupled to one or more pull wires 125 (also referred to as control lines) extending from the handle 110 internally through the guide catheter 105 to the distal end 115 of the guide catheter. For example, the pull wires 125 may extend through one or more internal lumens in the guide catheter 105. Actuation of the at least one control 120 may adjust the tensioning of the one or more pull wires 125 to steer the guide catheter 105 in a desired curvature and/or direction. FIG. 1 shows the handle 110 as having a single control 120 for providing steerability. Alternatively, a handle 110 may comprise more than one control 120 associated with any number of control lines in any suitable configuration, such as for rotation, axial translation, bending, or otherwise.

While control lines or wires are described at various points in this application, it should be understood that references made throughout this application to control lines or wires may refer to a single wire or plurality of wires including or made of steel, titanium alloy, aluminum alloy, nickel alloy, other metals, a shape-memory material (such as a shape-memory alloy or shape-memory polymer), an inorganic polymer, an organic polymer, ceramic, carbon materials, combinations thereof, or other flexible material with sufficient tensile strength. For example, a pull wire 125 (also referred to as "a control line 125") may be a steel cable or tungsten cable. In another example, a pull wire 125 may be a monofilament suture. In another example, a pull wire 125 may be a multifilament suture. In yet another example, a pull wire 125 may be a braided suture.

It is desirable for the guide catheter 105 to provide an adjustable distal end 115, which is capable of being positioned within a target body cavity in a desired orientation. The guide catheter 105 should have a large lumen diameter to accommodate the passage of a variety of devices, such as the various embodiments of the devices discussed herein—after, should have good wall strength to avoid kinking or collapse when bent around tight curves, and should have good column, tensile, and torsional strength to avoid deformation when the devices are passed through the lumen and torqued or translated.

The guide catheter 105 should provide for a high degree of controlled deflection at its distal end 115 in at least one axis, but should not take up significant lumen area to allow for passage of interventional devices therethrough, such as the devices discussed below. Further, the guide catheter 105 should be positionable in a manner which allows compound curves to be formed, for example curvature within more than one plane. Such manipulation should also allow fine control over the distal end 115 to accommodate anatomical variations within the same type of body cavity and for use in different types of body cavities.

The guide catheter 105 may comprise a main body made of or including a flexible material. The main body may be made of or include a variety of flexible materials, such as thermoplastic elastomers ("TPE"). In some embodiments, the main body may be a polyether block amide ("PEBA" or PEBAX®). The main body may have a constant durometer or may have varying durometer that varies along its longitudinal length or that varies in different portions of the main body.

For example, the main body of the guide catheter 105 may be made of or include a body material having a durometer of 25 D to 75 D. In another example, the main body of the guide catheter 105 may be made of or include a body material that has a durometer of about 45 D. In at least one embodiment, the body material may include PEBAX® 4533. In at least another embodiment, the body material may include PEBAX® 3533, available from Arkema Group of Colombes, France.

The guide catheter 105 preferably defines a central lumen, extending axially through its entire length or a substantial entirety of its length, through which other elements, such as the devices discussed herein, may be inserted for accessing a treatment site. The central lumen may also include a central lumen lining on an inner surface thereof. In some embodiments, the central lumen lining may be a protective material that protects the interior walls of the guide catheter 105 from damage due to another element of the elongated member moving through or within the central lumen.

In other embodiments, the central lumen lining may include a lubricious coating that reduces friction between the interior wall and another element of the elongated member moving through or within the central lumen. The central lumen lining may include PEB A, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the central lumen lining may include a plurality of PEBA materials having different durometers.

In other embodiments, the guide catheter 105 may also have an outer layer. In some embodiments, the outer layer may be made of or include a single material or may be made of or include different materials to impart different handling characteristics to the guide catheter 105. For example, the outer layer may be made of or include softer materials to promote flexibility of the guide catheter 105. In other examples, the outer layer may be made of or include stiffer materials to promote pushability and/or torqueability of the guide catheter 105.

In yet other examples, the outer layer may include lubricious materials to reduce friction between the guide catheter 105 and the body lumen of the patient. The outer layer may include PEBA, PTFEPEEK, other polymers, TPU polyethylene with pebble stone surface, silicone oil stainless steel, Nitinol, other metals, combinations thereof, or any suitable material. In at least one embodiment, the outer layer may include a plurality of PEBA materials having different durometers. The type and properties of the materials of the central lumen lining and/or the outer layer may vary along with a length and radial location of the guide catheter 105 as suitable.

In some embodiments, the outer layer of the guide catheter 105 may also include a radiopaque marker to improve visualization of the guide catheter 105 during a medical procedure. For example, the outer layer may include a radiopaque marker comprising or defined by barium sulfate (BaSO4), gold, platinum, platinum-iridium, iodine, other radiopaque materials, combinations thereof, or any other suitable material of the guide catheter 105. In at least one embodiment, one or more additional radiopaque markers may be longitudinally located at one or more intermediate locations along the length of the guide catheter 105.

Curves 140 of the guide catheter 105 may be formed by any suitable means. In some embodiments, one or more of the curves 140 are preset so that the curve 140 is formed by shape memory. For example, the guide catheter 105 may be comprised of a flexible polymer material in which a curve is preset by heating. When the guide catheter 105 is loaded on a guidewire, dilator, obturator, or introductory device, the flexibility of the guide catheter 105 can allow it to follow the shape or path of the introductory device for proper positioning within the body. When the introductory device is pulled back and/or removed, the guide catheter 105 can then resume the shape memory configuration which was preset into the guide catheter 105.

Alternatively, the curves 140 may be formed or enhanced with the use of one or more steering mechanisms. In some embodiments, the steering mechanism comprises at least one control wire or pull wire 125 attached to the guide catheter 105, wherein actuation of the steering mechanism applies tension to the at least one pull wire 125 whereby the curve 140 is formed. The pull wires 125 can extend through the central lumen or through individual lumens in the wall of the guide catheter 105.

It may be appreciated that more than one pull wire may extend through any given lumen. The presence of each pull wire allows a curvature of the guide catheter 105 in the direction of the pull wire. For example, when pulling or applying tension to a pull wire extending along one side of the guide catheter 105, the guide catheter 105 will bend, arc, or form a curvature toward that side. To then straighten the guide catheter 105, the tension may be relieved for recoiling effects, or tension may be applied to a pull wire extending along the opposite side of the guide catheter 105. In some embodiments, pull wires 125 can be directly attached to one or more features 131 on the catheter 105 to enable steering. Alternatively, the pull wires 125 can extend to and loop around the one or more features 131 on the catheter 125 so that a pull wire 125 extends distally from and returns to the handle 110. In some embodiments, it is preferred to use doubled loops with steerable catheters in the valve repair space.

Thus, in some embodiments, at least two pull wires are attached in diametrically opposed locations wherein applying tension to a first one of the pull wires curves the guide catheter 105 in a first direction and applying tension to a second one of the pull wires, i.e., the pull wire attached in the diametrically opposed location, curves the guide catheter 105 in a second direction opposite to the first direction. The diametrically opposed pull wires may be considered a set. Any number of sets may be present in a catheter, such as a guide catheter, to provide unlimited curvature directions.

In some embodiments, the steering mechanism can comprise at least four pull wires 125 wherein two of the at least four pull wires 125 are attached to the guide catheter 105 in diametrically opposed locations, and another two of the at least four pull wires 125 are attached to the guide catheter 105 in diametrically opposed locations, and may be aligned with or offset from the first set of pull wires.

In other words, the guide catheter 105 may include two sets of pull wires 125, each set functioning in an opposing manner as described. When the two sets of pull wires 125 are positioned so that each pull wire 125 is substantially radially 90 degrees apart, the guide catheter 105 may be curved so that the distal end 115 is directed from side to side and up and down, respectively.

In other embodiments, the steering mechanism comprises at least three pull wires 125, each pull wire 125 substantially symmetrically positioned approximately 120 degrees apart. When tension is applied to any of the pull wires 125 individually, the guide catheter 105 is curved in the direction of the pull wire 125 under tension. When tension is applied to two pull wires 125 simultaneously, the guide catheter 105 is curved in a direction between the pull wires 125 under tension. Additional directions may also be achieved by various levels of tension on the pull wires 125. It may be appreciated that any number, combination, and arrangement of pull wires may be used to direct the catheters, such as a guide catheter, in any desired direction. It will be appreciated that the above description similarly may apply to a delivery, imaging, or another type of catheter.

In some embodiments, a portion of the guide catheter 105 can comprise one or more articulating members. In this case, the at least one pull wire 125 is attached to one of the articulating members so that the curve 140 is formed by at least some of the articulating members. Each pull wire 125 is attached to the guide catheter 105 at a location chosen to result in a particular desired curvature of the guide catheter 105 when tension is applied to the pull wire 125.

For example, if a pull wire 125 is attached to the most distal articulating member of a series of articulating members, applying tension to the pull wire 125 will compress the articulating members proximal to the attachment point along the path of the pull wire 125. This results in a curvature forming in the direction of the pull wire 125 proximal to the attachment point. It may be appreciated that the pull wires 125 may be attached to any location along the guide catheter 105, and are not limited to attaching to articulating members. Typically, the articulating members comprise interfitting domed rings as described in at least U.S. Pat. No. 8,409,273, granted Apr. 2, 2013, incorporated herein in its entirety by reference, but may have any suitable shape.

It may also be appreciated that curves 140 in the guide catheter 105 may be formed by any combination of mechanisms. For example, a portion of the guide catheter 105 could form a curve 140 by shape memory, while a different portion of the guide catheter 105 could form a curve 140 by actuation of a steering mechanism.

The steering mechanisms may be actuated by manipulation of one or more actuators 108 located on the handle 110. The handle 110 can be connected with the proximal end 112 of the guide catheter 105 and remains outside of the body of the patient so as to be manipulated by a practitioner or user. One or more actuators or controls 120 can be provided on the handle 110 and may have any suitable form, including buttons, levers, knobs, switches, toggles, dials, or thumbwheels, to name a few. When pull wires 125 are used, each actuator 108 may apply tension to an individual pull wire or a set of pull wires. The handle 110 may also include one or more locking mechanisms configured to interface with, and selectively lock into place, one or more of the controls 120.

In at least one embodiment, the handle 110 includes at least one control 120 for actuating and/or adjusting one or more components of a device 130. As shown in FIG. 1, the device 130 is configured to extend beyond the distal end 115 of the guide catheter 105. In at least one embodiment, the device 130 is routable through the guide catheter 105 and retractable into the guide catheter 105, for example, through a central body lumen thereof, as discussed above.

The at least one control 120 may control extension from, and retraction into, the guide catheter 105 of the device 130. Additionally or alternatively, the at least one control 120 may be configured to provide selective actuation of the device 130. The at least one control 120 may be operatively connected to one or more additional elements of the device 130. The device 130 is shown here in generic form as a dashed line, and therefore represents any of the device or unit embodiments described herein.

II. Various Embodiments

Figure 2:
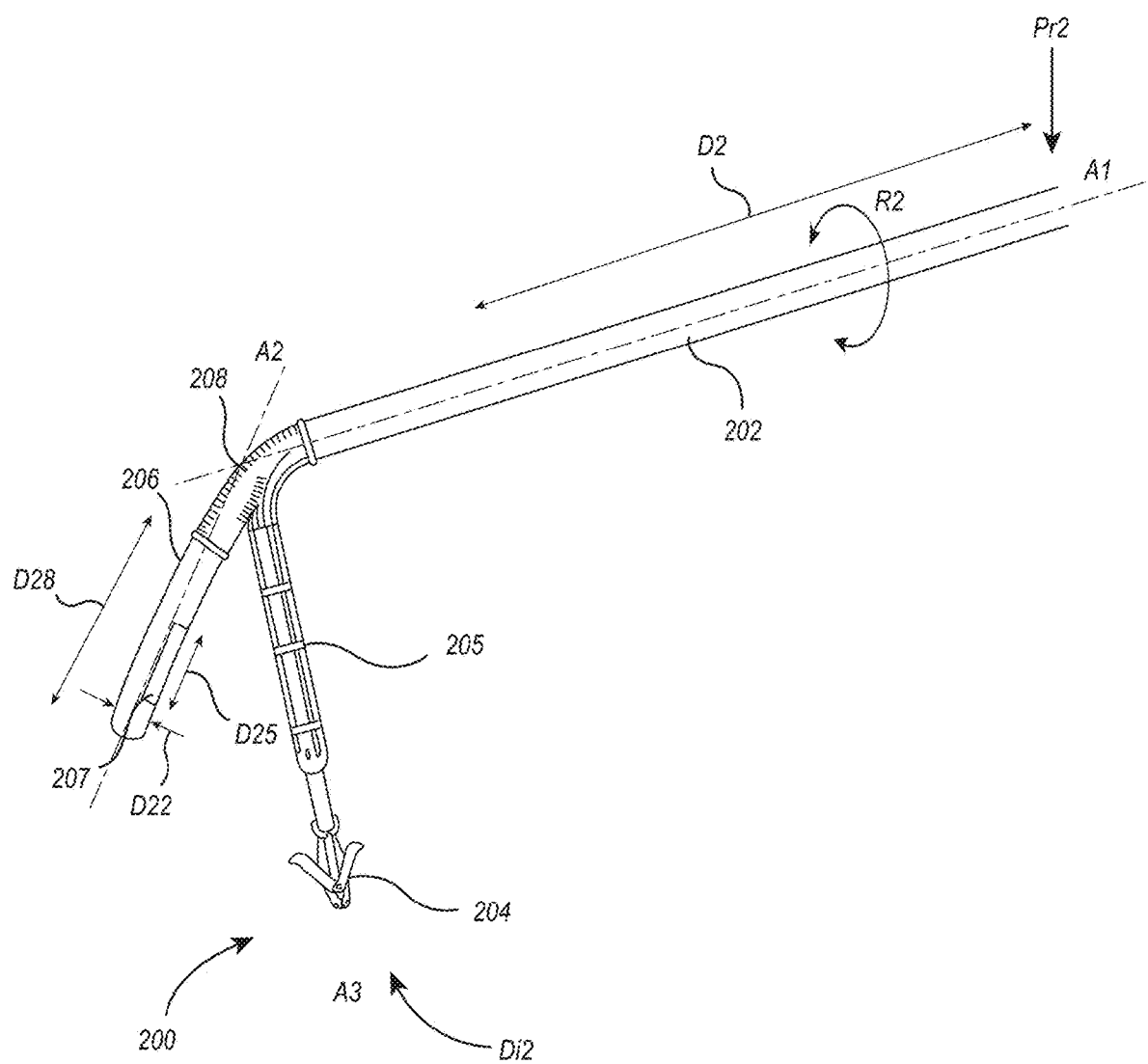
FIG. 2 illustrates in perspective view a distal end region of an integrated imaging and device deployment platform according to an embodiment.

FIG. 2 illustrates in perspective view a distal end region of an integrated imaging and device deployment platform 200 (which corresponds to the system 100 of FIG. 1) according to an embodiment. The platform 200 may advantageously combine imaging modalities and device delivery modalities in a manner that facilitates better imaging and navigation of a patient's anatomy, such as a vascular system, a heart chamber, or otherwise.

The platform 200 may be formed as a delivery system as described above regarding the embodiment of FIG. 1 and may advantageously integrate an imaging modality and a device deployment modality as described herein. The platform 200 may comprise a catheter 202 configured to both deliver a device 204 and to support an imaging unit 206.

The device 204 may be a therapeutic device intended for minimally invasive therapies and procedures, such as a MitraClip® fixation device and accompanying steerable catheter and deployment device available from Abbott Vascular of Santa Clara, CA, USA, and as described in at least U.S. Pat. No. 7,736,388, filed Jan. 16, 2007, U.S. Pat. No. 7,226,467, filed May 19, 2003, U.S. Pat. No. 7,666,204, filed May 19, 2003, U.S. Pat. No. 7,563,267, filed May 19, 2003, and U.S. Pat. No. 8,500,761, filed Dec. 11, 2009, each of which is incorporated herein in its entirety by reference.

In other embodiments, the device 204 may be a LAA occluder device such as the Amplatzer Amulet® LAA Occluder available from Abbott Cardiovascular of Santa Clara, CA, USA, and as described in at least U.S. Pat. No. 8,034,061, filed Jul. 12, 2007, incorporated herein in its entirety by reference. While the above devices have been suggested and described, it will be understood that the disclosure is not limited thereto, and other transcatheter devices such as atrial-septal defect ("ASD") occluders, ventricular septal defect ("VSD") occluders, pulmonic valve replacement devices, aortic valve repair/replacement devices, radiofrequency ("RF") ablation catheters, cryo-ablation catheters, annuloplasty device, implantable pacemakers, or any other suitable device may be used. For example, the device 204 may be a cutting mechanism, such as a rotating drill device for use in an atherectomy procedure, a balloon catheter and/or a stent for a balloon angioplasty procedure, or otherwise.

The device 204 may be supported within or on the catheter 202 by any suitable means and may be deployed by any suitable means. In embodiments, the device 204 is deployed using a delivery unit 205 configured as a delivery catheter configured to cooperate with a tether that is detachably coupled to a portion of the device 204, as described in U.S. Pat. No. 7,666,204, filed May 19, 2003. For example, the catheter 202 may cooperate with a suitable steerable guide handle, and delivery catheter handle to navigate and deploy the device 204 as described above regarding FIG. 1.

The delivery unit 205 may be manipulated by the delivery catheter handle to position and orient the device 204 through a body lumen at a desired location, for example, at a mitral valve or at the left atrium appendage. The platform 200 may be rotated through a rotation direction R1 and/or translated in an axial direction D1 as part of navigating a body lumen. Additionally, the catheter 202 may be able to bend in at least two planes as well.

The imaging unit 206 may be supported in or on the catheter 202 by a connecting portion 208. By integrating the imaging unit 206 and the device 204 in the integrated imaging and device deployment platform 200 as described herein, the catheter 202 may include a single catheter that is used for both imaging and device delivery, simplifying a procedure for which the integrated imaging and device deployment platform 200 is used. The platform 200 allows the separate catheters to support the imaging unit 206 and the device 204 need not be independently maneuvered and navigated through the patient's anatomy as is done in current/existing procedures.

In embodiments, the imaging unit 206 may comprise an ICE catheter, a mapping catheter, a magnetic-, impedance- or dielectric-based sensing or imaging catheter, optical coherence tomography ("OCT"), photo-acoustics-based imaging catheter, intravascular imaging system, optical fiber-based imaging system, or other suitable imaging modality. In some embodiments, the imaging catheter is an intra-cardiac echocardiography imaging device.

The imaging unit 206 may further comprise or cooperate with one or more sensors 207 arranged on the imaging unit 206. As described herein, the sensors 207 may be any suitable sensors such as optical fibers, OCT, dielectric imaging, electro-magnetic sensing, magnetic sensing, impedance-based sensing, capacitive sensing, or microelectromechanical systems ("MEMS")-based sensing and may be configured to provide real-time position information.

In embodiments where the imaging unit 206 comprises an ICE catheter, the ICE catheter may be an ICE catheter such as a ViewFlex™ Xtra ICE Catheter available from St. Jude Medical of St. Paul, MN, USA. In embodiments where the imaging unit 206 comprises a mapping catheter, the mapping catheter may be a mapping catheter such as an Advisor™ HD Grid Mapping Catheter, Sensor Enabled™ available from Abbott Cardiovascular of Santa Clara, CA, USA. While the above embodiments of the imaging unit 206 have been shown and described, it will be appreciated that the imaging unit 206 may be any suitable imaging modality.

The connecting portion 208 of the catheter 202 may be formed of any suitable material, such as polymeric material, metallic material, hybrid materials, combinations thereof, or otherwise. In embodiments, the imaging unit 206 extends generally coaxially with the delivery unit 205 within and/or along at least a portion of a length of the catheter 202, for example from a proximal end of the catheter 202.

The imaging unit 206 may extend along the second axis A2 from the connecting portion 208 by a distance D28. The distance D28 may, in embodiments, be between 1 and 50 mm, preferably between 10 and 30 mm, and in embodiments approximately 15 mm. The imaging unit 206 may have a thickness or diameter D22, which in embodiments may be between 1 and 30 French gauge, preferably between 5 and 15 French gauge, and in embodiments approximately 8 French gauge. A window or sensor 207 may have a length D25 extending along the axis A2 that may be between 1 and 20 mm, preferably between 3 and 10 mm, in embodiments approximately 5 mm.

The imaging unit 206 and the delivery unit 205 may, in embodiments, comprise distinct catheters extending coaxially within the catheter 202. The distinct catheters of the imaging unit 206 and the delivery unit 205 may extend side-by-side and/or parallel to one another along at least a portion of the length of the catheter 202. The catheter 202 may function as a sheath surrounding the distinct catheters of the imaging unit 206 and the delivery unit 205.

In other embodiments discussed in greater detail herein, the catheter 202 may be substantially integral or continuous with one of the imaging unit 206 or the delivery unit 205, with the other of the imaging unit 206 or delivery unit 205 extending through an interior of the catheter 202 and separating therefrom at a distal end portion of the platform 200.

In other embodiments, the imaging unit 206 may be proximal to the device or distal end of the delivery unit 205 and may extend out at an angle to the catheter 202 of the integrated imaging and device deployment platform 200. Extension and angulation of the imaging unit 206 can be further controlled by a translating handle mechanism that is pushed or pulled by the user to adjust the angle of the imaging view, for example, by applying tension to pull wires attached to the imaging unit 206.

In other embodiments, the imaging unit 206 may not extend out of the catheter 202, and may rather be maneuvered by the user by rotating about the main axis A1 of the catheter 202 via a rotation mechanism or pivot at a desired angle using a suitable mechanism.

A distal end $Di_2$ of the imaging unit 206 may be configured to separate and bend away from the delivery unit 205 at a distal end of the catheter 202, i.e., proximate the device 204. This arrangement may advantageously simplify the navigation and use of the platform 200 while retaining the ability to maneuver each of the imaging unit 206 and the delivery unit 205, particularly near a target anatomy such as a heart valve or structure, as needed. In other embodiments, the imaging unit 206 and the delivery unit 205 separate from the catheter 202 which is unitary at the connecting portion 208.

The connecting portion 208 may extend generally from an axis A1 along which the catheter 202 extends in a suitable navigation or imaging direction or axis A2. By contrast, the device 204 and the delivery unit 205 may extend in a suitable delivery direction or axis A3.

In embodiments, the axes A1, A2, A3 may be aligned during moments as the catheter 202 is navigated through a body lumen of the patient to a desired location. In other embodiments, the axis A2 of the imaging unit 206 may be offset by a distance from the axis A3 of the delivery unit 205 so as not to occlude the imaging unit 206 or disrupt the delivery unit 205. As the platform 200 is navigated to a desired location, the imaging unit 206 may advantageously provide real-time information, in embodiments coupled with one or more additional imaging modalities such as a pre-acquired CT image or 3D rendering of the anatomy, or embedded sensor information, to assist a practitioner in accurately navigating and deploying the catheter 202 and the device 204.

The imaging unit 206 may be configured to rotate or bend so as to view an anatomical feature, such as the inter-atrial septum. The position of the inter-atrial septum puncture relative to a valve plane is important for steering and positioning of the device 204. In existing systems, the position of the inter-atrial septum puncture relative to the valve plane is only estimated prior to puncturing the septum. After the puncture is made and the catheter is advanced by a user therethrough into the left atrium, the puncture hole can stretch or deform due to the stiffness of the catheter as it is maneuvered. This can lead to substantial error and damage.

By providing an imaging unit 206 in an integrated imaging and device deployment platform 200 according to embodiments of the disclosure, a user has improved knowledge of the actual position of the puncture hole, allowing the user to maneuver the catheter 202 with increased precision. The provision of an integrated imaging and device deployment platform 200 according to the embodiments further allows a user to learn a device deployment technique more quickly, and facilitates improved results across a range of septum types, including thin, thick, and fibrous septums.

Figure 3A:
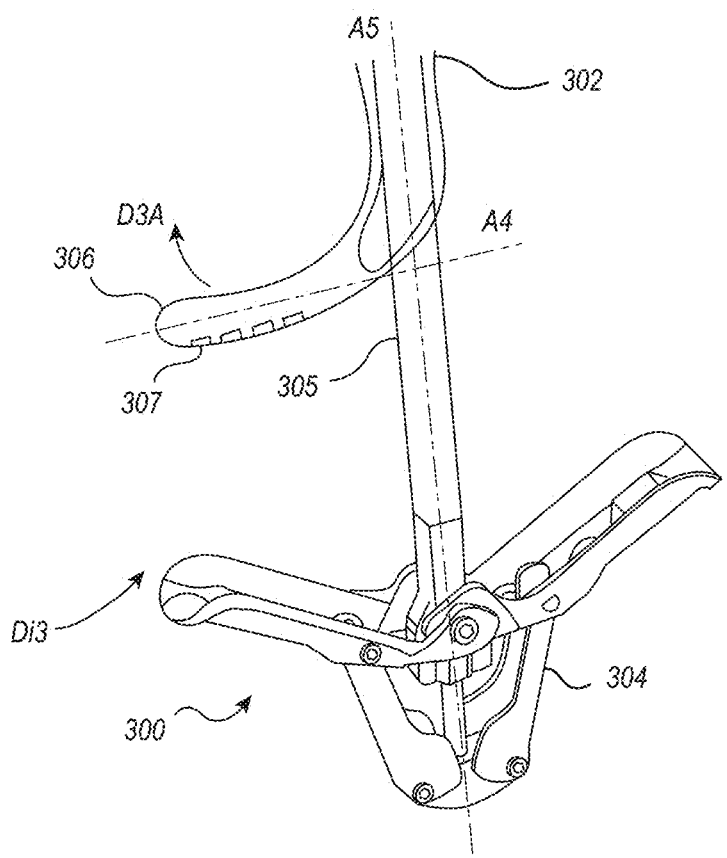
FIG. 3A illustrates in perspective view an imaging modality, delivery modality, and device for the integrated imaging and device deployment platform according to the embodiment of FIG. 2.
Figure 3B:
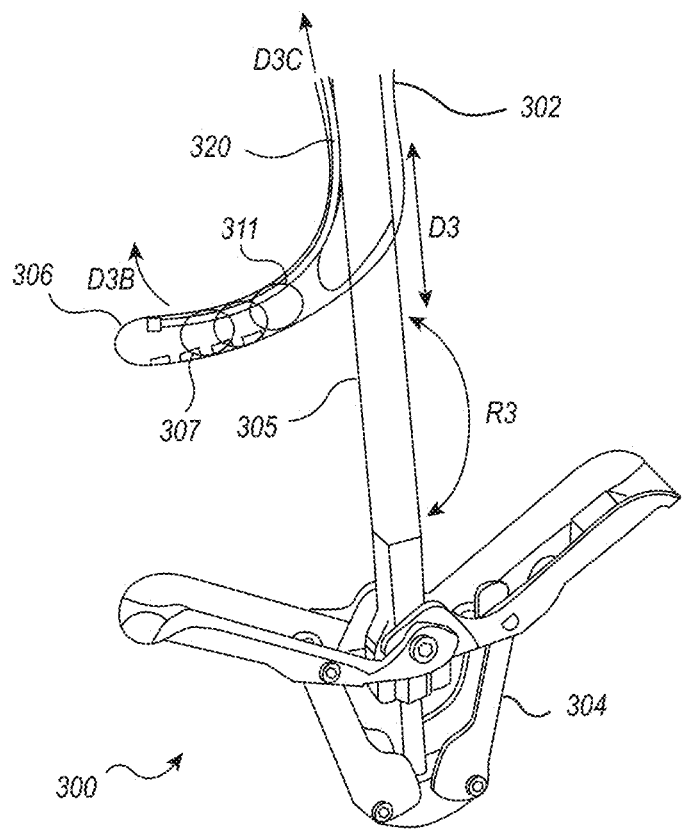
FIG. 3B illustrates in perspective view the imaging modality, delivery modality, and device of FIG. 3A according to another embodiment.
Figure 3C:
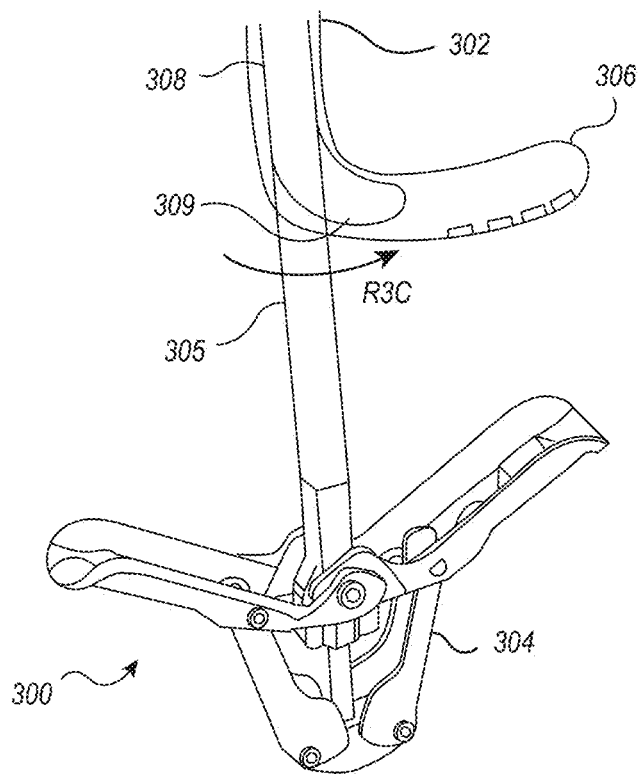
FIG. 3C illustrates in perspective view the imaging modality, delivery modality, and device of FIG. 3A according to another embodiment.

As seen in FIGS. 3A-3C, an integrated imaging and device deployment platform 300 (which corresponds to the system 100 of FIG. 1)) according to another embodiment is shown in perspective view. The platform 300 may comprise a device 304, such as a therapeutic device suitable for a minimally invasive therapy, as described above in regards to FIGS. 1 and 2. In the depicted embodiment, the device 304 is a MitraClip® fixation device, but it is to be understood that the device 304 may be any suitable device, including medical devices or otherwise. The platform 300 may also comprise an imaging unit 306 as described above.

The device 304 may be supported on a catheter 302 by a delivery unit 305 which may extend from the catheter 302. In embodiments, the delivery unit 305 may be a catheter formed substantially continuously with the catheter 302 or may be formed separately from the catheter 302 and attached to the catheter 302 by suitable means. The catheter 302 may extend generally longitudinally about an axis A5.

The delivery unit 305 may extend about the axis A5, or may extend about a distinct and/or offset axis as shown and described regarding the embodiment of FIG. 2. In the depicted embodiment, the delivery unit 305 may comprise a distinct delivery catheter configured to extend through an interior lumen of the catheter 302, which may be continuous and integrated with an imaging catheter forming the imaging unit 306.

A cut-out portion 308 of the catheter 302 provides for separation of and relative moment between the imaging unit 306 and the delivery unit 305. The cut-out portion 308 may define any suitable profile, size, or shape, and the delivery catheter of the delivery unit 305 may extend therethrough to extend from the interior lumen of the catheter 302. In the embodiment of FIG. 3C, the cut-out portion 308 may advantageously extend about only one side or half of the catheter 302, such that the opposing side or half of the catheter 302 maintains a continuously extending surface substantially or entirely closed to the outside.

The cut-out portion 308 may be formed of PEBAX® or other suitable material. The cut-out portion 308 may be configured to facilitate rapid exchange catheter construction. The cut-out portion 308 may further be reinforced with at least one layer of braided steel material (not shown) that extends along or through at least part of a thickness of the material, such as PEBAX®. The layer of braided steel may advantageously provide structural support so as to form a mechanical hinge and hole structure. While braided steel has been described, it will be appreciated that the reinforcing layer may comprise tubular laser-cut stainless steel, braided stainless steel wire or ribbon, or made of similar construction with other metals such as Titanium or Nitinol.

In embodiments, the delivery unit 305 may comprise a distinct catheter extending coaxially through a substantial entirety of the catheter 302 such that the delivery unit 305 may extend through the cut-out portion 308 at a distal end $Di_3$ of the catheter 302 to diverge to a desired degree from the imaging unit 306. In embodiments, the imaging unit 306 may be a continuation of the catheter 302. The cut-out portion 308 may define a profile 309 that allows for a desired degree of movement between the imaging unit 306 and the delivery unit 305. The degrees of movement between the imaging unit 306 and the delivery unit 305 involve tilting at an angle with respect to the main axis A5 of the platform 200, rotating in a plane at an angle to the catheter 302, and/or angling and/or rotating at a desired angle with respect to a landmark on the platform 300 or device component (e.g. a clip arm of the device 204).

The imaging unit 306 may be twisted or twirled across a substantially 180-degree span to enable visualization of the entire valve being treated by a Mitraclip® fixation device. Rotation from the central axis R3C may be at least up to 90 degrees and may be larger than 90 degrees in embodiments. If the rotation is acute (i.e. less than 90 degrees), an imaging unit 306 as shown in FIG. 3C may be rotated as a rigid body about the axis A5.

It will be understood that while one imaging unit 306 has been shown and described, multiple imaging units 306 and/or multiple delivery units 305 may be employed as suitable. For example, in an embodiment, at least two imaging units 306 may be provided, allowing a practitioner to simultaneously visualize both leaflets and orifices of an anatomical structure.

The embedded sensors 307 may be arranged on a surface of the imaging unit 306, along the catheter 302, along a portion of the delivery unit 305, or at any suitable location along the platform 300. In embodiments, the embedded sensors 307 may be arranged on an interior surface of the cut-out portion 308 or the imaging unit 306, which may comprise a distinct imaging catheter such as an ICE catheter as described herein.

The platform 300 may further comprise an imaging unit 306 extending separately from the delivery unit 305 and the device 304. The imaging unit 306 may comprise one or more sensors 307 extending along at least a portion of the imaging unit 306. In an embodiment, the sensors 307 are configured to provide position-related information. In embodiments, the sensors 307 are embedded within at least a portion of a thickness of a wall of one or more catheters of the platform 300. A distal end portion of the imaging unit 306 may extend about an axis A4 spaced a distance and an angle from the axis A5. The space and angle between the axes A4, A5 may vary during use of the platform 300. The imaging unit 306 may be an ICE catheter and may be a rapid-exchange-style ICE probe.

For example, during a preliminary insertion and navigation stage of use, the angle and distance between the axes A4, A5, and the imaging unit 306 and the delivery unit 305 may be at a minimum to maintain a reduced width and profile of the platform 300 as the platform 300 is navigated through body lumens. During a subsequent navigation stage or during a deployment stage of use, the angle and distance between the axes A4, A5, and the imaging unit 306 and the delivery unit 305 may increase as necessary and/or suitable to enable a practitioner to properly image and detect a patient's anatomy.

As described above regarding the embodiment of FIG. 2, the imaging unit 306 may be configured to rotate, bend, and/or translate relative to the catheter 302 and/or the delivery unit 305 as suitable. For example, the imaging unit 306 may be configured to rotate by any suitable number of degrees relative to the delivery unit 305, such as up to substantially 180 degrees.

The imaging unit 306 may define a separate catheter unit extending generally continuously from the catheter 302 at a predetermined location. The imaging unit 306 and the delivery unit 305 may be formed of a same material as the catheter 302 and may have a same diameter as the catheter 302. In embodiments, the material and/or diameter of the imaging unit 306 and the delivery unit 305 may vary from each other and from the catheter 302 as suitable. For example, the imaging unit 306 and the delivery unit 305 may have a reduced diameter compared to the catheter 302 to minimize a profile of the platform 300.

One or more of the imaging unit 306 and the delivery unit 305 may comprise a material such as PEBAX®. The material may have a higher durometer and may comprise through at least a part of a thickness thereof a braided metal structure or laser-cut tubing structure cut with a diamond pattern, slit-cut pattern, or stent-like pattern as a reinforcement structure.

The platform 300 may translate in an axial direction D3 and may rotate in a rotation direction R3 to properly navigate and position the device 304 relative to the patient's anatomy. In embodiments, the imaging unit 306 may also be actuated, translated, moved, rotated, bent, or otherwise moved relative to the delivery unit 305 by any suitable mechanism, as described herein.

In the embodiment of FIGS. 3A-3C, the catheter 302 may comprise at least one pull wire 320 extending through an interior of the catheter 302 and into the imaging unit 306. A distal end of the pull wire 320 may secure at a suitable location in the imaging unit 306, such as at a distal end of the imaging unit 306, as shown in FIG. 3B. The pull wire 320 may be formed of any suitable material, including metal such as steel or tungsten, polymer, synthetic material, or otherwise, as described above. In certain embodiments, the pull wire 320 is formed of steel or tungsten to facilitate sufficient force and to avoid problematic creep.

The pull wire 320 may be actuated by a practitioner to move the imaging unit 306 axially and/or radially to a desired position and configuration relative to the delivery unit 305. A proximal end of the pull wire 320 may be pulled by the practitioner in an axial direction D3C towards a proximal end of the catheter 302. In embodiments, the proximal end of the pull wire 320 may be secured and manipulated by a suitable catheter delivery handle as described in at least U.S. Pat. No. 7,666,204, filed May 19, 2003, and as described above regarding FIG. 1.

As the pull wire 320 is pulled or manipulated in the direction D3C, the imaging unit 306 may be pulled or bent in a direction D3B, particularly at a distal end of the imaging unit 306. While the distal end of the pull wire 320 is shown as extending and securing to the distal end of the imaging unit 306, it will be understood that the pull wire 320 may extend a shorter distance into the imaging unit 306.

Pull wires may be routed through one or more steering rings 311 that establish a consistent pulling position around the circumference of the imaging unit 306 and should cause bending deformation in the catheter that occurs proximal to the imaging unit 306. The one or more steering rings 311 may be arranged on a surface and/or in a thickness of the imaging unit 306 catheter, and may be formed of any suitable material, including steel, tungsten, polymer, composite material, or otherwise. The steering rings 311 may comprise any suitable feature for guiding or cooperating with an action of the pull wire 320, including notches, grooves, rings, apertures, or otherwise through which the pull wire may pass or fit.

The imaging unit 306 may be formed from a material having resilient properties and/or a shape-memory feature such that as the practitioner releases or stops pulling the pull wire 320, the imaging unit 306 may relax and return to a previous configuration. The delivery unit 305 may also be configured to extend or retract independently of the imaging unit 306.

This may be beneficial in situations where the imaging unit 306 is in a desired location or configuration, and extending or retracting axially the delivery unit 305 may serve to deploy the device 304 or better navigate the device 304 relative to the patient's anatomy, such as relative to a heart valve or structure. This may also be beneficial in that the practitioner need not manipulate the entirety of the platform 300 including the imaging unit 306, but rather may specifically target and manipulate the delivery unit 305 as needed.

By providing an imaging unit 306 in proximity to a device and delivery unit such as a MitraClip® fixation device as described and shown in the integrated imaging and device deployment platform embodiments, a practitioner may advantageously obtain imaging of, for example, a valve leaflet and device interaction with a better image quality than transesophageal echocardiography ("TEE") combined with hemodynamics. Additionally, the integrated imaging and device deployment platform embodiments further provide soft-tissue information such as tissue thickness, tissue calcification, tissue tears or defects, dynamic tissue contact, i.e. a valve leaflet resting on a clip arm of the device 304, a gripper of the device 304 coming in contact with the valve leaflet, a change in mobility of a valve leaflet due to device 304 contact, and/or a change in hemodynamics with the device-tissue interaction, that fluoroscopy as used in existing procedures cannot provide.

The provision of the imaging unit 306 in cooperation with an integrated imaging and device deployment platform 300 as described herein advantageously may allow for improved estimation of an orifice area and improved doppler flow imaging. Doppler imaging may be performed using the imaging unit 306 to visualize regurgitant flow during systole. Regurgitant flow may be quantified by pre- and post-procedure regurgitant flow profile (vena contracta), or by flow volume/magnitude of backflow using proximal isovelocity surface area ("PISA"). Continuous-wave doppler can be used for estimation of pressure gradients to judge a severity of a valve occlusion created by or during implanting a device 304.

Providing an imaging unit 306 in close proximity to a delivery unit 305 as facilitated by the disclosed embodiments advantageously provides a better assessment of conditions that may arise during various procedures. For example, it has been found that the disclosed embodiments which provide a closer proximity of the imaging and delivery units 306, 305 as well as the ability to articulate the catheter may provide improved assessment of double orifice that may be created by the device, such as a MitraClip® fixation device, during a valve repair procedure.

In embodiments, the imaging unit 306 may be configured to articulate in a rotational direction relative to the delivery unit 305 in addition to being configured to articulate in an axial direction relative to the delivery unit 305 as described above. By rotating the imaging unit 306 relative to the delivery unit 305, a practitioner can advantageously provide necessary visualization from various rotational angles and positions of the patient's anatomy, the configuration of the device, or the interaction of the device with the anatomy.

In an embodiment in which the device 304 is a therapeutic device for a cardiac procedure, a practitioner may rotate the imaging unit 306 in a rotation direction R2C relative to the delivery unit 305 and the device 304. The imaging unit 306 may be configured to rotate substantially 360° about the catheter 302.

The platform 300 may be configured to allow a practitioner to torque or rotate the catheter 302 such that the imaging unit 306 rotates through the rotation direction R3C about the delivery unit 305 as needed. In embodiments, the imaging unit 306 provides real-time imaging information to the practitioner such that the practitioner can accurately position the imaging unit 306 relative to the delivery unit 305 and the catheter 302.

For example, the practitioner may rotate the imaging unit 306 during a procedure to visualize different parts of the anatomy corresponding to different procedure steps. The imaging unit 306 may be rotated mid-procedure to visualize the insertion of a second leaflet of the device 304 after the insertion of the first leaflet. To do so, the practitioner may perform a sweep of one of the orifices of the anatomy, such as a heart valve, or may stop at an intermediate point perpendicular to the device 304.

Because of the effects of blood flow within the patient's anatomy, the catheter 302, the imaging unit 306, and the delivery unit 305, for example, may be formed from materials, optionally comprising frictional features, with a minimum level of friction configured to apply texture to an internal diameter ("ID") of the imaging unit 306 and/or the outer diameter ("OD") of the catheter 302. Alternatively, the catheter 302, imaging unit 306, and delivery unit 305 may comprise splined bumps, detents, surface finishes, or other frictional features along the ID or OD, respectively, configured to resist small forces.

This construction of the platform 300 may advantageously provide stabilization of the platform against blood flow forces, particularly if and when the blood flow is dynamic and when the platform 300 directly contacts the patient's anatomy. While a user may need to overcome the resistance of the frictional features, such as splined bumps, when maneuvering the platform 300, the provision of frictional features stabilizes the platform 300. In some embodiments, in addition to or instead of the friction features, the securement of the position of the imaging unit 306 relative to the catheter 302 can also be accomplished through fastening features 132, such as set screws, threaded fasteners, such as bolts, etc., biased or spring loaded fasteners, combinations and/or modifications thereof between the device (such as one or more of the delivery unit 304 and/or the imaging unit 306) and the catheter, such as the catheter 302, at the device handle 110 or as part of the controls 120 shown in FIG. 1.

This can allow the practitioner to visualize the orifice and any remaining regurgitant flow or the surface area of the valve. In embodiments, forward flow gradient can be estimated locally during diastole using targeted imaging of the orifice using the imaging unit 306 throughout the cardiac cycle.

By providing an integrated imaging and device deployment platform 300 as shown and described, a practitioner may advantageously navigate, image, and deploy a device using an integrated platform, which simplifies a device insertion, navigation, and delivery procedure, provides improved imaging and location information, and mitigates the risks of existing imaging modalities including X-ray exposure and contrast injection-related risks.

Figure 4:
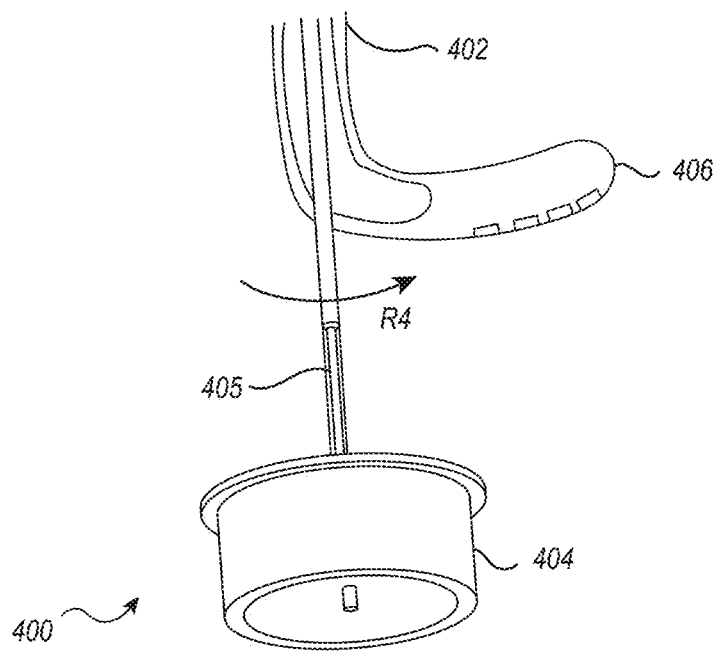
FIG. 4 illustrates in perspective view an imaging modality, delivery modality, and device for the integrated imaging and device deployment platform of FIG. 2 according to another embodiment.

Turning now to FIG. 4, an integrated imaging and device deployment platform 300 is depicted. The platform 400 may comprise as described in previous embodiments a catheter 402 attached to and/or cooperating with an imaging unit 406 and a delivery unit 405 supporting an expandable and releasable implant device 404 (also referred to as "the device").

The device 404 may be a left atrial appendage occluder device, such as the Amplatzer Amulet® LAA Occluder available from Abbott Cardiovascular of Santa Clara, CA, USA. The imaging unit 406 may comprise an ICE imaging catheter or any other suitable imaging unit. The imaging unit 406 may be configured to provide confirmation to a practitioner of the position, trajectory, deployment and/or placement of the device 404, for example, by establishing and confirming a direction of delivery of the device 404. Additionally, the imaging unit 406 may advantageously provide an estimation of a diameter of the LAA, helping a practitioner to properly fit the device 404 to the patient's anatomy.

In use, the imaging unit 406 may be configured to facilitate resolution of diameter change of the device 404 when inserted into the left atrial appendage. This may confirm to the practitioner that sufficient radial outward fixation force is present in the device 404. The imaging unit 406 may further help the practitioner to visualize the deployment process of the device 404 for any issues.

As seen, the delivery unit 405 may comprise a catheter extending from the catheter 402. The imaging unit 406 may likewise comprise a second catheter 408 generally extending continuously with the catheter 402. The second catheter 408 of the imaging unit 406 catheter may have a smaller diameter than a diameter of the catheter 402 of the delivery unit 405, which may be configured to extend internally of the catheter 402.

Figure 5A:
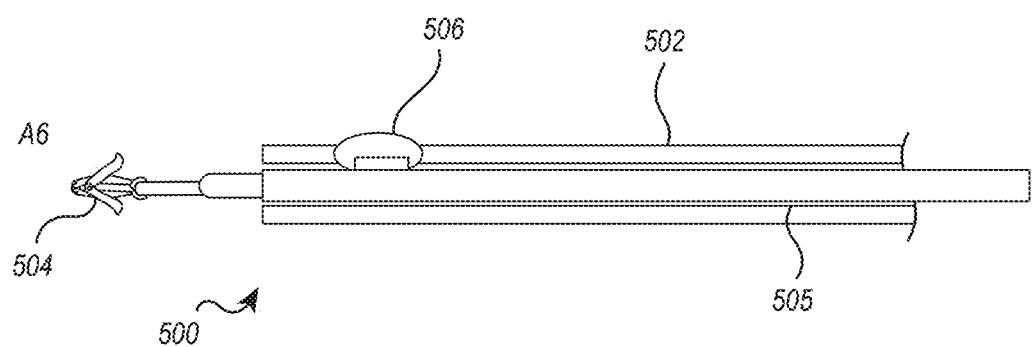
FIG. 5A illustrates in a side elevational view an integrated imaging and device delivery platform according to another embodiment.
Figure 5B:
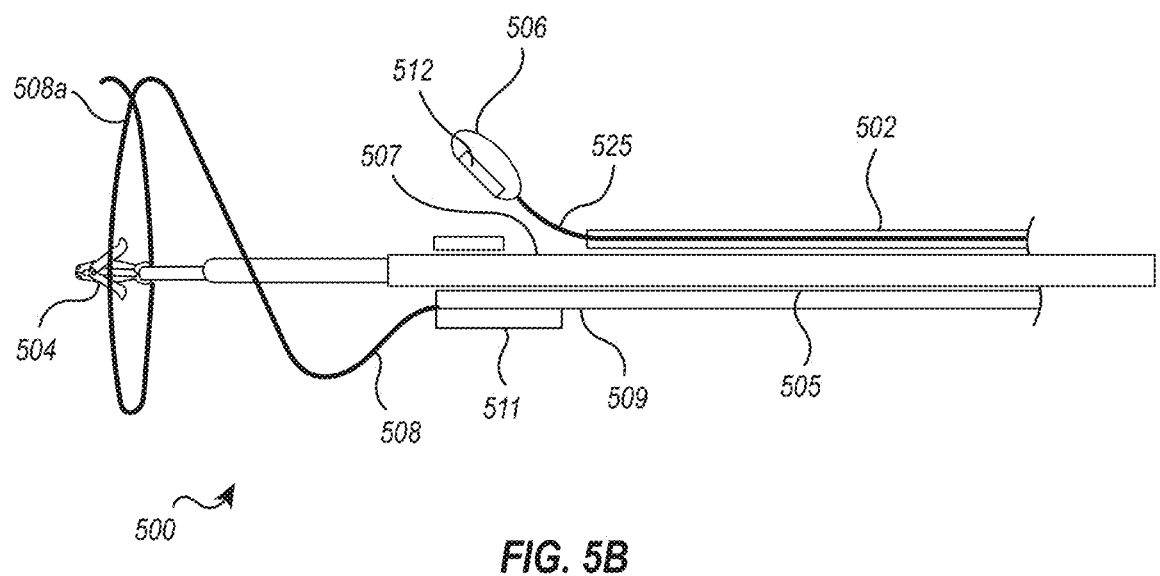
FIG. 5B illustrates in a side elevational view the platform of FIG. 5A.

Turning now to FIGS. 5A and 5B, an integrated imaging and device delivery platform 500 (which corresponds to the system 100 of FIG. 1) according to another embodiment is shown in elevational side view. The platform 500 may extend substantially in an elongate manner about a longitudinal axis A6. The platform 500, as described in the foregoing embodiments, may comprise a catheter 502, through and/or from which a delivery unit 505 and an imaging unit 506 may attach and extend for integrated use of the imaging unit 506 and the delivery unit 505 during a procedure. The imaging unit 506 may be any suitable imaging modality as described herein. The platform 500 may further comprise embedded sensors (not shown) as described in the foregoing embodiments.

The delivery unit 505 may be configured to deliver a device 504 as described in the foregoing embodiments, such as a therapeutic device including a MitraClip®. The delivery unit 505 may be a distinct catheter extending through a central lumen of the catheter 502, and may be configured to axially extend therefrom to deliver the device 504.

The imaging unit 506 may advantageously be provided in a recess 507 defined by a surface of the catheter 502, such as an outer surface of the catheter 502. The imaging unit 506 may be configured to fit within the recess 507 to minimize a profile of the platform 500, particularly during an insertion and/or navigation stage of a procedure.

The imaging unit 506 may be attached to the platform 500 by a pull wire 525. The pull wire 525 may advantageously comprise electronic wiring or cables allowing one or more signals obtained by the imaging unit 506 to be transmitted to the user. The pull wire 525 may also allow the user to manipulate a position of the imaging unit 506 out of the recess 507 and into a suitable position for capturing one or more images or position-related information.

In a retracted position as shown in FIG. 5A, the imaging unit 506 may be releasably secured within the recess 507 such that a sensor or window 512 faces inwardly regarding the platform 500. In the extended position as shown in FIG. 5B, the imaging unit 506 may be extended so a position such that the sensor or window 512 faces a desired direction, such as toward a distal end of the platform 500. This may allow the imaging unit 506 to capture one or more images of the device 504.

In embodiments, the platform 500 may further comprise a loop 508 extending from an aperture 509 defined within the catheter 502, such as between a portion 511 of the sleeve and an outer surface of the catheter 502. The loop 508 may define one or more revolutions 508a about the platform 500. The portion 511 may be provided at a distal end of the catheter 502, or at any suitable location.

The platform 500 may be configured such that steering and navigation of the platform 500 by a user actuates extension of the imaging unit 506. For example, as a user actuates a delivery unit 505 to translate axially from the catheter 502, the platform may be configured to automatically extend the imaging unit 506.

FIGS. 6A-6F illustrate an alternative embodiment of an integrated imaging and device delivery platform 600 (also referred to as "the platform") according to the present disclosure. The platform 600 may advantageously facilitate a low profile for insertion and navigation through a patient's anatomy by providing an imaging unit 606 as shown and described herein. The imaging unit 606 may have a hinged connection 613 to a catheter 602 of the platform 600, such that the imaging unit 606 may toggle between a retracted position (shown in FIGS. 6A and 6C and one or more extended positions (shown in FIGS. 6B, 6D, 6E, and 6F).

The imaging unit 606 may comprise a window or sensor 612. In the retracted position of FIG. 6A, the window or sensor 612 may be rotated to face inwardly of the catheter 502. In the extended positions of FIGS. 6B, 6D, 6E, and 6F, the window or sensor 612 may be rotated to face outwardly of the catheter 502, such as toward a distal end of the platform 600. The window or sensor 612 may have a configuration facilitating and capturing a field of view 610, which varies based on an angle of extension of the imaging unit 606. In embodiments, the field of view 610 may be positioned to include the device 604, helping a user or practitioner to properly position and deploy the device 604.

The imaging unit 606 may be attached to the platform 600 by one or more electronic cables or wires 609 and/or one or more pull wires 625. The pull wires 625 may serve to actuate the imaging unit 606 between different positions. In embodiments, the imaging unit 606 may be actuated to an extended position by an action of the catheter 602 or the delivery unit 605 extending from the catheter 602 to delivery or position the device 604.

Figure 6A:
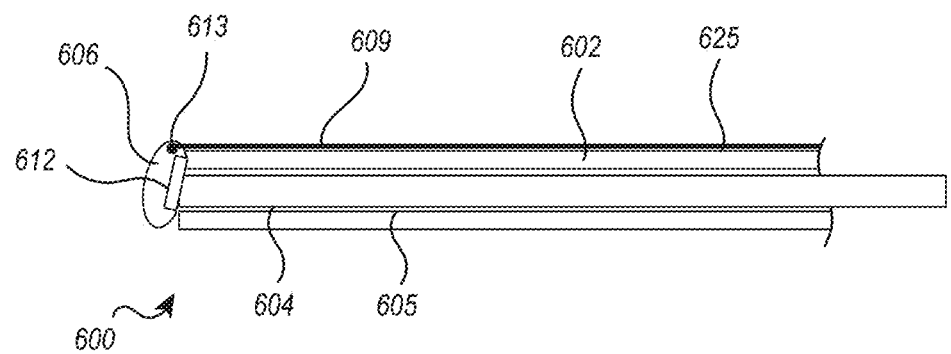
FIG. 6A illustrates in side elevational view an integrated imaging and device delivery platform according to another embodiment.
Figure 6B:
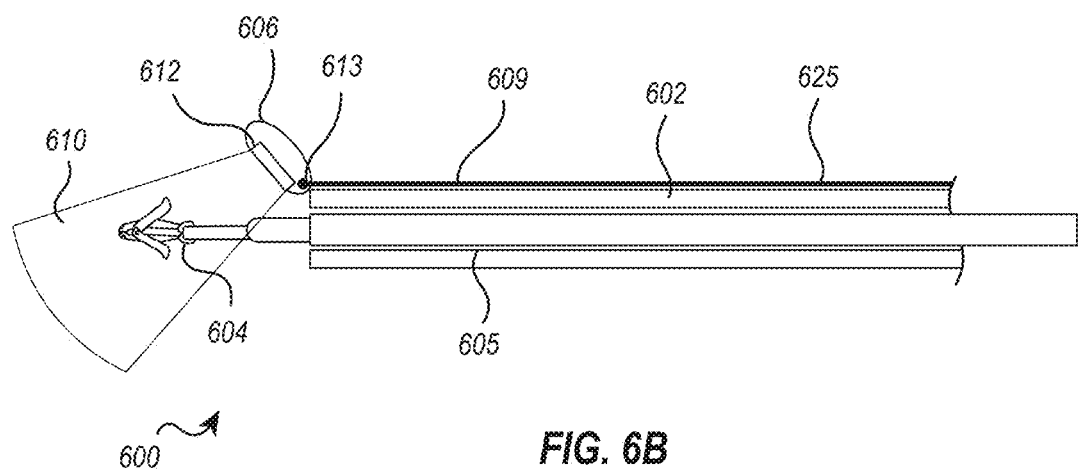
FIG. 6B illustrates in a side elevational view the platform of FIG. 6A in an extended configuration.
Figure 6C:
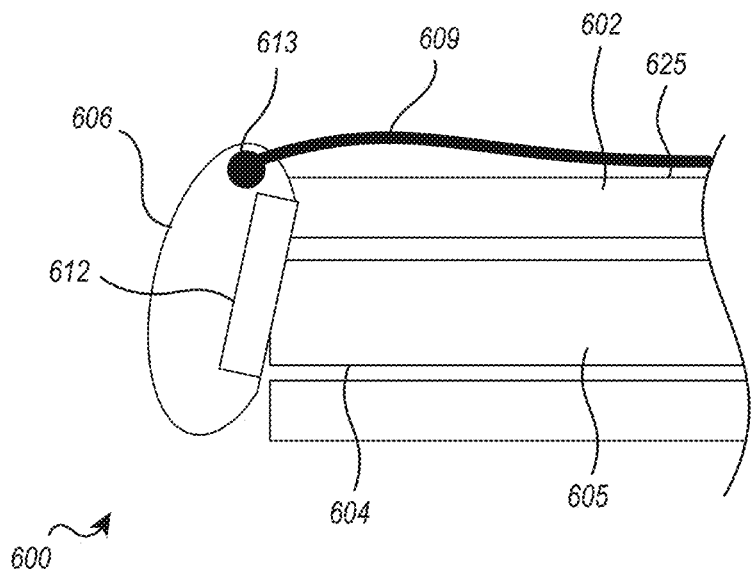
FIG. 6C illustrates in a side elevational view the platform of FIG. 6A in a retracted configuration.
Figure 6D:
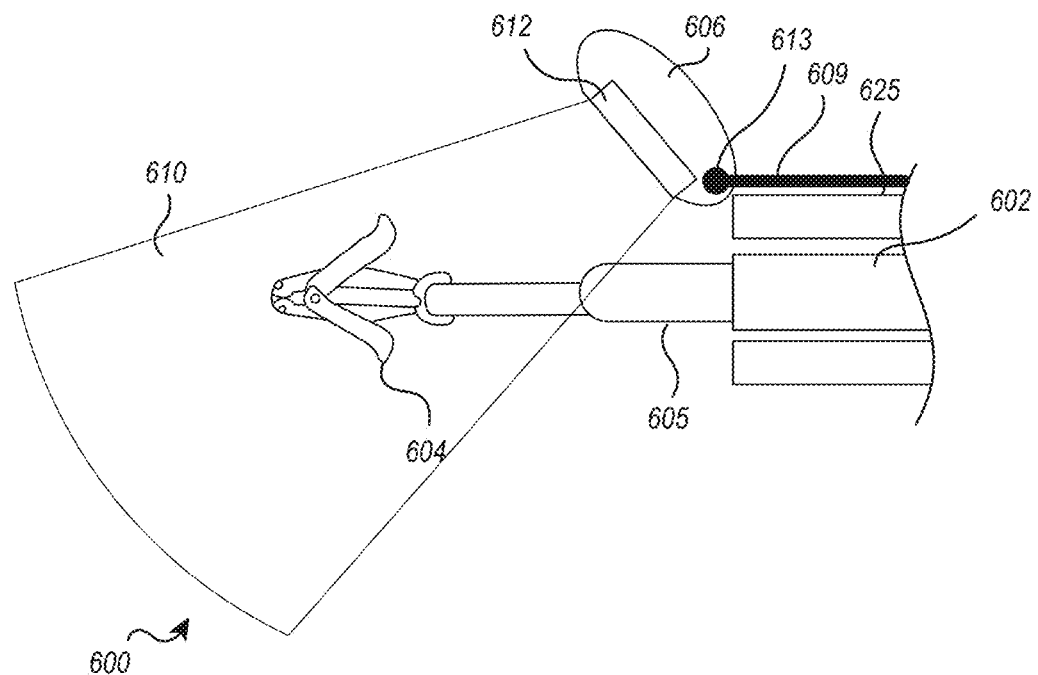
FIG. 6D illustrates in a side elevational view the platform of FIG. 6A in an extended configuration.
Figure 6E:
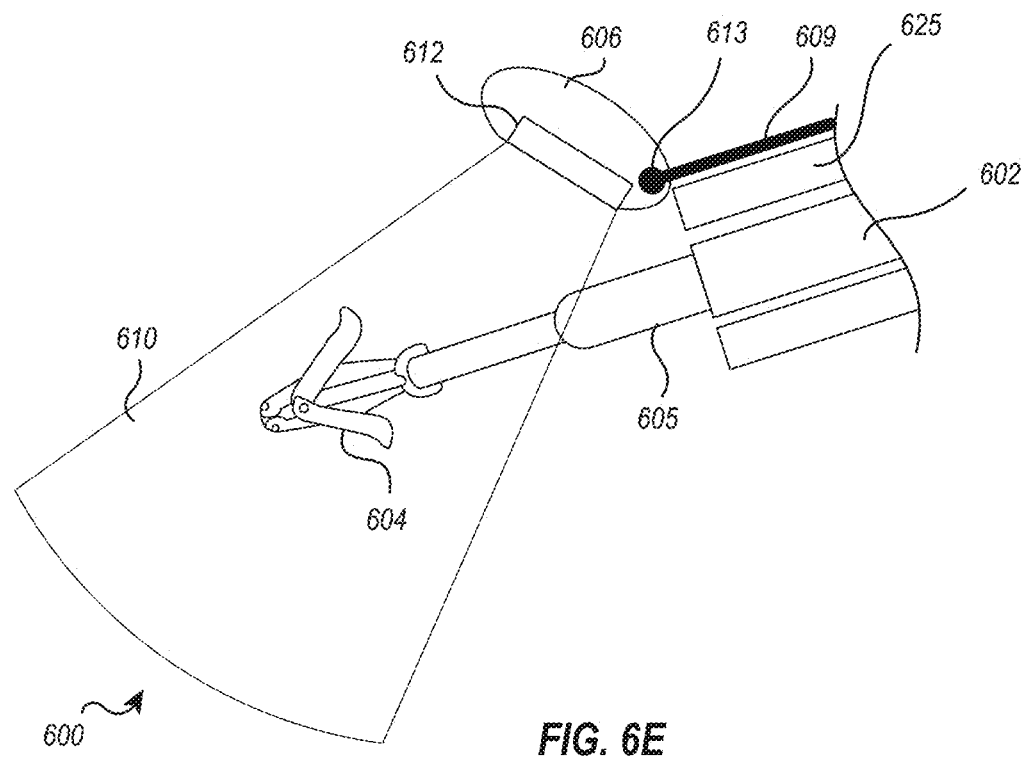
FIG. 6E illustrates in a side elevational view the platform of FIG. 6A in an extended configuration.
Figure 6F:
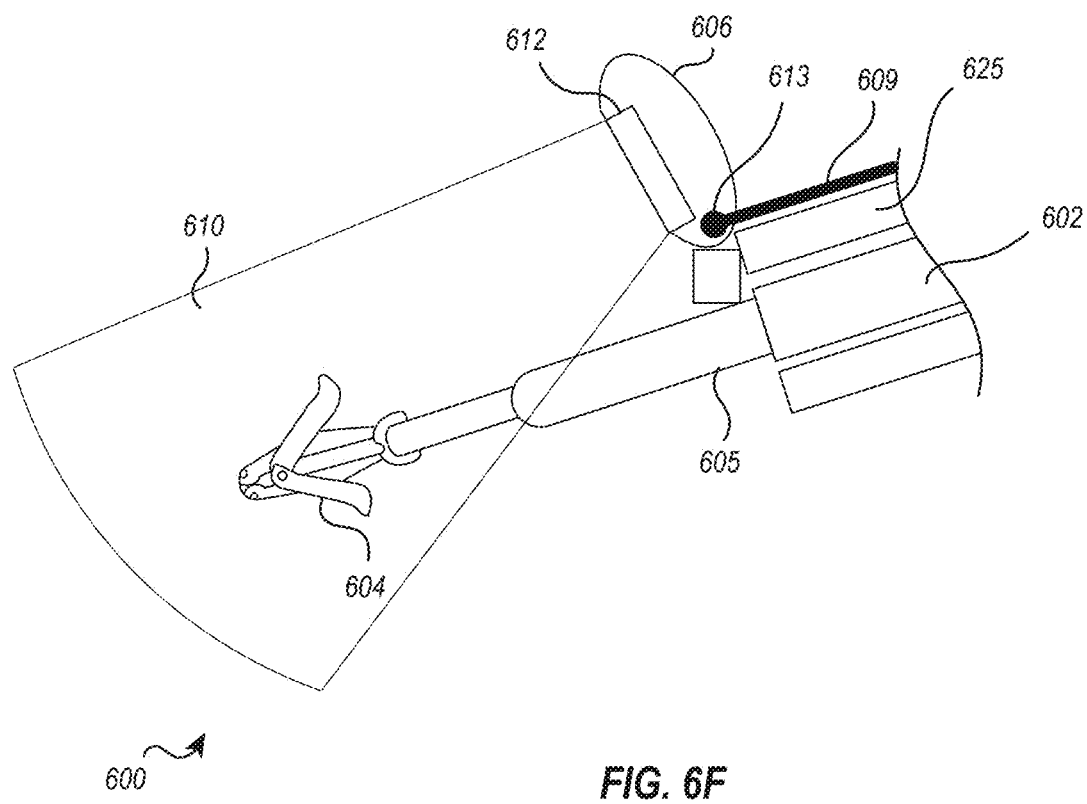
FIG. 6F illustrates in a side elevational view the platform of FIG. 6A in an extended configuration.

As shown in FIGS. 6E and 6F, the field of view 610 may be pivoted by the user to extend substantially below the device 604 (as shown in FIG. 6E) or substantially above the device 604 (as shown in FIG. 6F). The field of view 610 may be pivoted by any suitable mechanism, such as the pull wire 625. In embodiments, the pull wire 625 may be configured to lock the field of view 610 in a particular angle or degree of extension, such as while the user deploys or delivers the device 604.

Figure 7A:
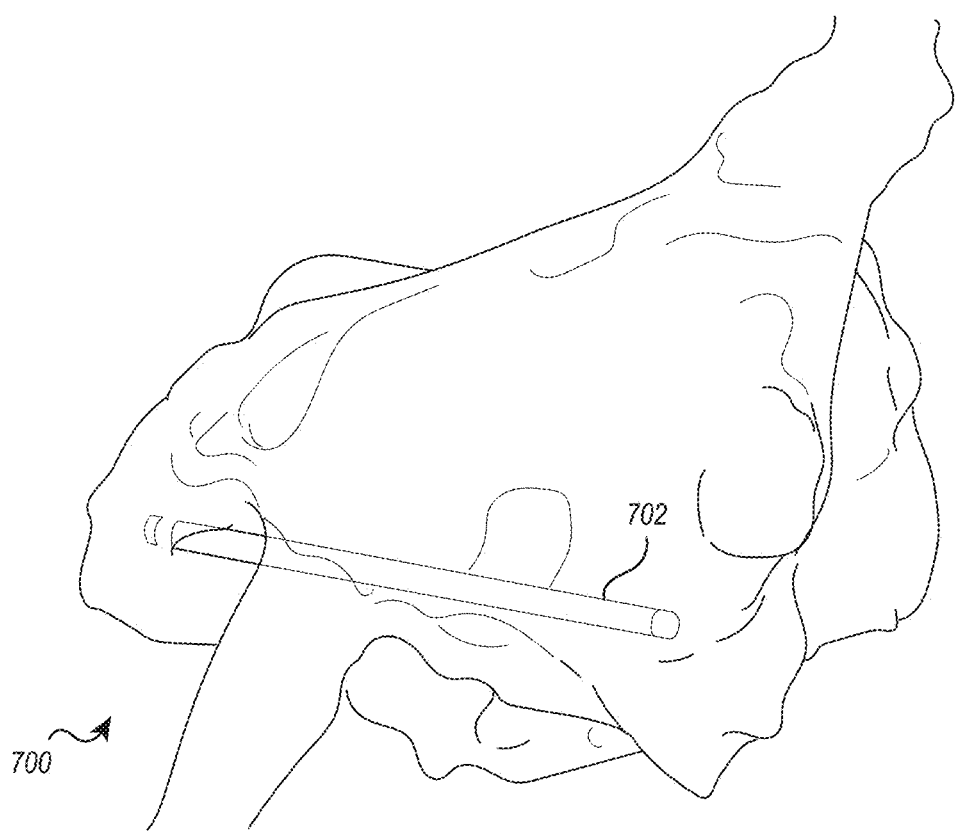
FIG. 7A illustrates a rendered 3D visualization of an anatomy of a patient using the integrated imaging and device deployment platform and method according to an embodiment.
Figure 7B:
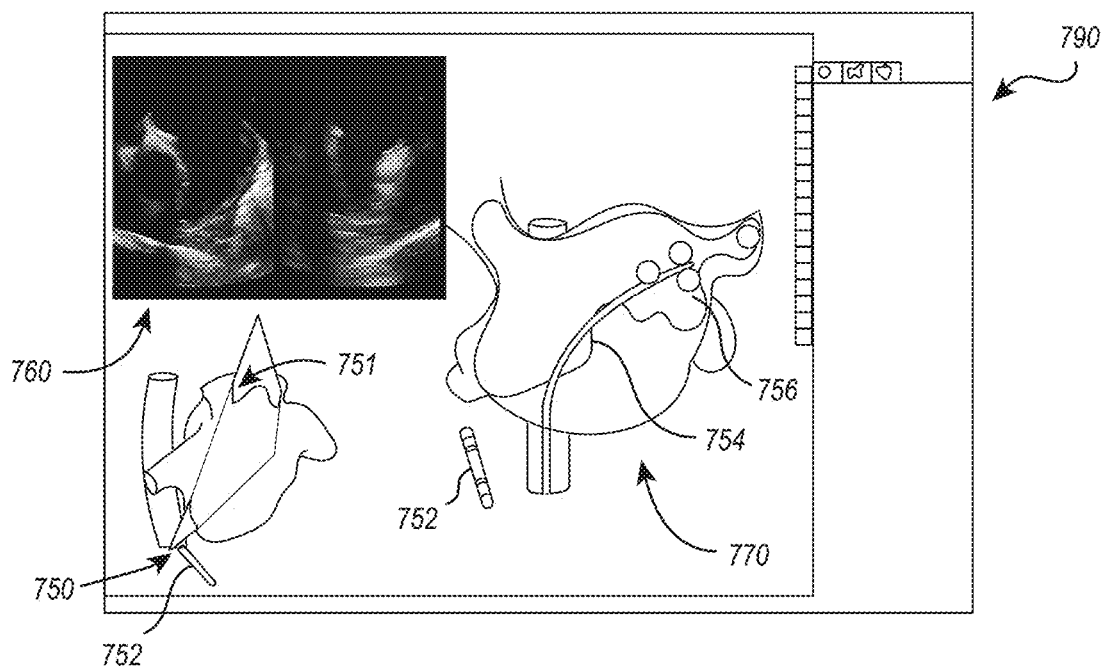
FIG. 7B illustrates a rendered 3D visualization of an anatomy of a patient using the integrated imaging and device deployment platform and method according to another embodiment.

Turning now to FIGS. 7A and 7B, FIG. 7A is a depiction 700 of a device or catheter 702 comprising at least one embedded sensor, the catheter 702 being inserted into a patient's body and detected and visualized in 3D space using a magnetic or impedance imaging method, similar to one provided by Abbott's EnSite™ system, with or without a pre-acquired CT or intra-procedural sensor-based mapping or 3D echocardiography, dielectric, or other electro-magnetic imaging system.

The pre-acquired data may provide gross anatomical landmarks whereas real-time tissue dynamics (such as valves) or detailed anatomical information may be provided only for a sub-volume of interest. The depiction 700, which may be presented in real-time during a procedure to the practitioner, provides immediate and dynamic visualization of the patient's anatomy and the position of the device or catheter 702 relative to the anatomy. Using the depiction 700, the practitioner may accurately guide and navigate the catheter 702 so as to deploy a device, such as a therapeutic device, to a particular anatomical feature such as a mitral valve or LAA.

The depiction 700 may identify and show one or more anatomical landmarks and/or close-up views. In a mitral valve repair and valve replacement procedure, identification of one or more of a valve plane, valve size, leaflet length, leaflet coaptation length, leaflet prolapse or flail height, leaflet tip-to-tip gap (if incomplete), and residual leaflet may be shown.

For LAA treatment, landmarks for one or more of an LAA position, location, and approximate diameter may be identified and shown to confirm that a selected device, such as an LAA occluder device, will fit properly without creating too much radial force or too little interference with the anatomy. For ablation catheters and related procedures, landmarks suitable for maze pulmonary vein isolation procedures may be identified and shown. In these cases, pulmonary veins need to be visualized to help the user target the sites for ablation to reduce arrhythmia.

FIG. 7B comprises a plurality of depictions 750, 760, 770 of a detected imaging catheter 752 and a detected device 754 inside a 3D rendering of a chamber of a heart. The depictions 750, 760, 770 may be shown on a user interface 790.

The first depiction 750 shows an imaging plane 751 transecting the heart. The detected imaging catheter 752 is shown as the practitioner navigates and guides the imaging catheter and an associated device to a desired location in the heart. The second depiction 760 shows a detected device 754 inside a heart chamber as seen from the perspective of the imaging plane 751. The second depiction 760 may be obtained using the imaging catheter 752.

The third depiction 770 shows the detected imaging catheter 752 and the detected device 754 relative to the heart as seen through the imaging plane 751. The third depiction 770 may comprise one or more features 756 annotated on the third depiction 770. The features 756 may indicate landmarks with which the device 754 or the imaging catheter 752 is required or encouraged to interact during a procedure. The depictions 750, 760, 770 may be configured to display multiple devices 754 in a single depiction as suitable. The user interface 790 may be configured to allow a user to toggle on and off the one or more landmarks such that a user may focus on only the landmarks that are pertinent to a particular procedure or step of a procedure. The user interface 790 may automatically generate and display the landmarks.

The combination of the depictions 750, 760, 770 as enabled by the embodiments of an integrated imaging and device deployment platform, including multiple imaging modalities including a 3D space visualization using a magnetic or impedance method and information available from an embedded sensor such as an ICE catheter, advantageously provides a detailed rendering of the patient's anatomy without the need for an X-ray based imaging modality. The patient's anatomy is thereby accurately detailed to a practitioner in real-time without sacrificing imaging results and while reducing the risks to a patient concomitant with existing imaging methods.

The following discussion now refers to a number of methods and method steps/acts that may be performed. Although the method steps/acts may be discussed in a certain order or illustrated in a flow chart as occurring in a particular order, no particular ordering is required unless specifically stated, or required because a step/act is dependent on another step/act being completed prior to the step/act being performed.

Figure 8A:
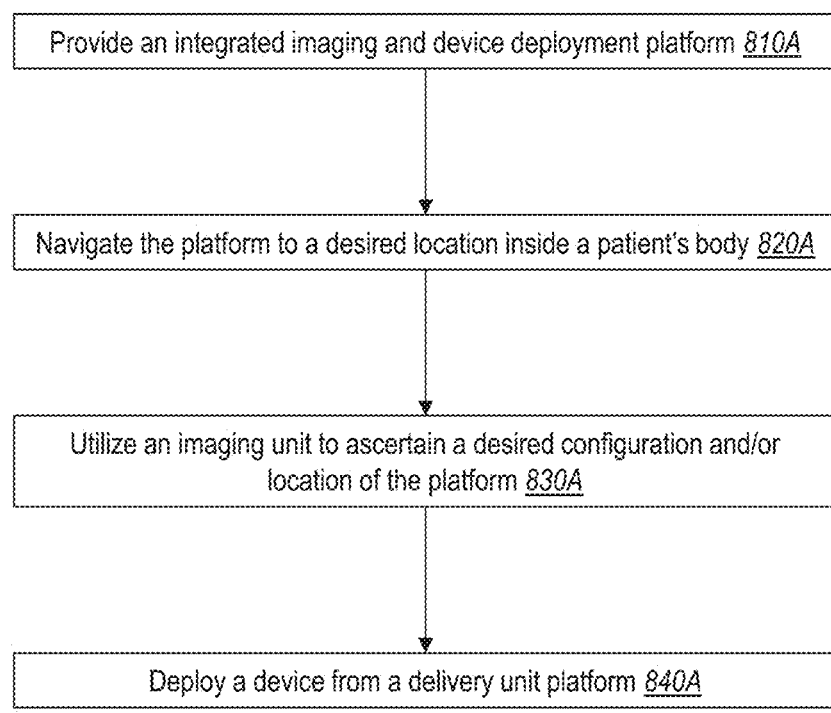
FIG. 8A illustrates a flowchart of an example method for deploying a device from a delivery unit platform.

FIG. 8A illustrates a flowchart of an example method 800A according to an embodiment of the disclosure. The method 800A may include one or more of the following: providing an integrated imaging and device deployment platform according to the embodiments (810A); navigating the platform to a desired location inside a patient's body (820A); utilizing an imaging unit to ascertain a desired configuration and/or location of the platform (830A); and deploying a device from a delivery unit (840A).

Figure 8B:
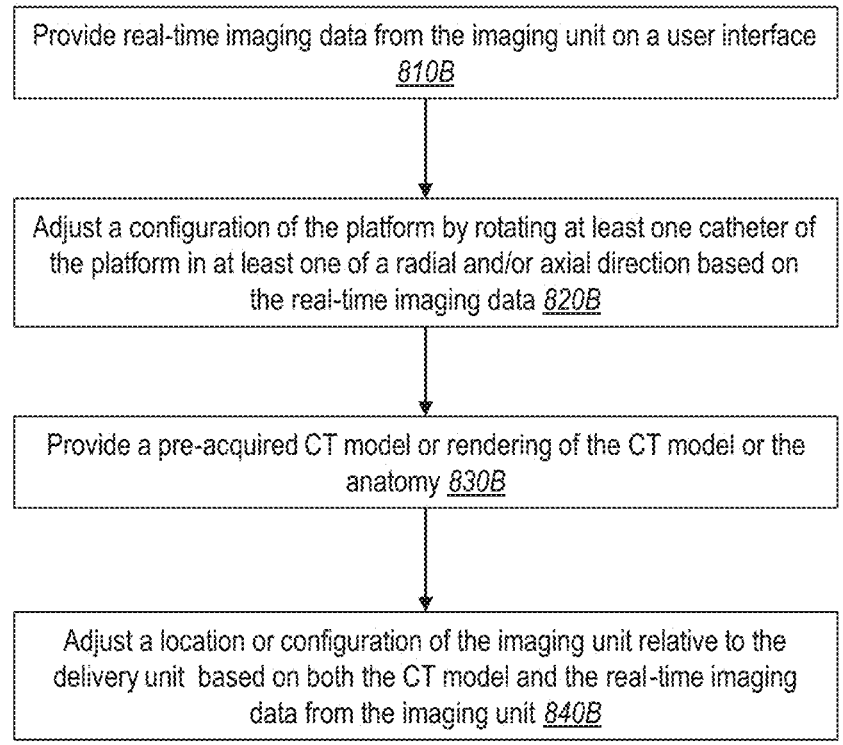
FIG. 8B illustrates a flowchart of an example method for utilizing an imaging unit to ascertain a desired configuration and/or location of a delivery unit platform.

In some embodiments, utilizing the imaging unit to ascertain a desired configuration and/or location of the platform (830A) may further include additional sub-actions. FIG. 8B illustrates a flowchart of an example method 800B for utilizing an image unit to ascertain a desired configuration and/or location of the platform, which corresponds to 830A of FIG. 8A. The method 800B may include providing real-time imaging data from the imaging unit on a user interface (810B); and adjusting a configuration of the platform by rotating at least one catheter of the platform in at least one of a radial and/or axial direction based on the real-time imaging data received from the imaging unit (820B).

In addition, the method 800B may further include a preliminary step of providing a pre-acquired CT model or rendering of the CT model or the anatomy at a user interface (830B). The preliminary step may alternatively or in addition provide a 3D rendering generated from a mapping catheter. In some embodiments, the CT model and the 3D rendering generated from the mapping catheter are overlaid and integrated together. The integrated image is then shown in the user interface (e.g., the user interface shown in FIG. 7B). The method 800B may further include adjusting a location or configuration of the imaging unit relative to the delivery unit based on both the CT model and the real-time imaging data from the imaging unit (840B).

Figure 9:
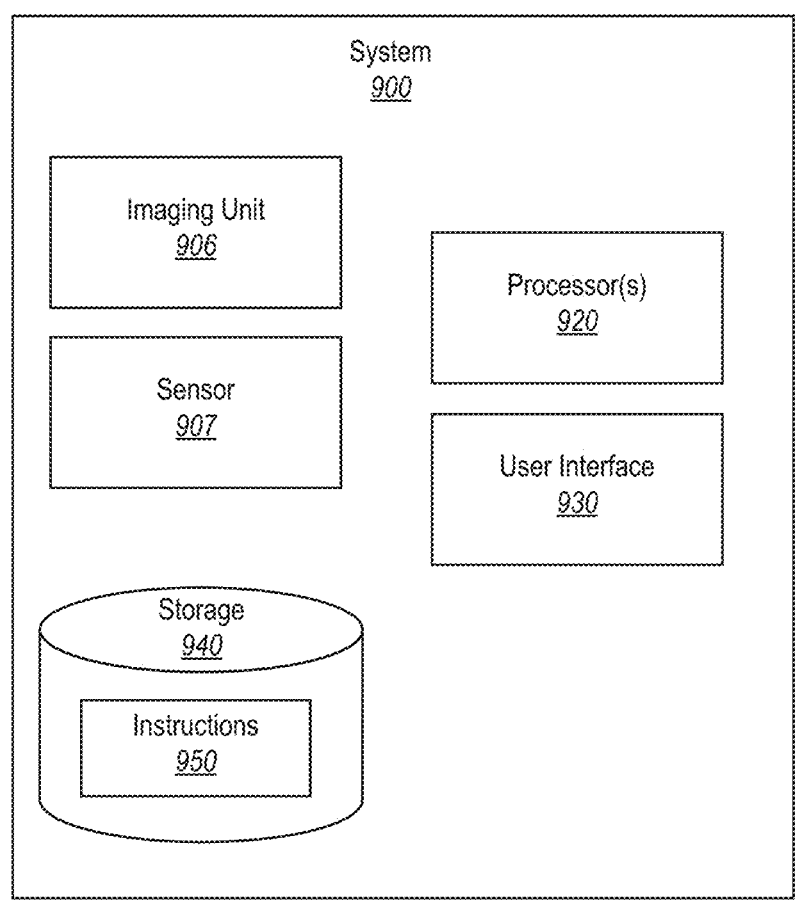
FIG. 9 is a diagram of components of an embodiment of an integrated imaging and device deployment platform.

Turning to FIG. 9, components of an embodiment of an integrated imaging and device deployment platform 900 are depicted in a diagram. In embodiments, the integrated imaging and device deployment platform 900 may comprise one or more processors 920 and one or more computer-readable hardware storage devices 940. The storage devices 940 include computer-executable instructions 950 stored thereon that are executable by the one or more processors 920 to cause the integrated imaging and device deployment platform 900 to capture information including images using at least one imaging unit 906 and/or at least one sensor 907 and/or to produce a user interface 930 on which real-time information from the at least one imaging unit 906 and/or the at least one sensor 907 may be displayed.

The instructions 950 may cause the platform 900 to combine the real-time information from the at least one imaging unit 906 and/or the at least one sensor 907 with information including a pre-acquired imaging model or information, such as a CT image, model, or rendering. By providing the integrated imaging and device deployment platform 900, the imaging unit 906 and at least one sensor 907 may be utilized with a delivery device, a catheter, and a device, such as a therapeutic device as described herein, to navigate, image, and delivery a device during a procedure.

By providing an integrated imaging and device deployment platform and method according to the embodiments of the present disclosure, the problem of existing imaging modalities being potentially harmful to a patient are mitigated, while the accuracy and details of an image rendering provided to a practitioner are improved.

III. Further Example Embodiments

Following are further example embodiments of the invention. These are presented only by way of example and are not intended to limit the scope of the invention in any way.

Embodiment 1. An integrated imaging and device deployment platform, comprising at least one catheter, at least one delivery unit, and at least one imaging unit. the at least one delivery unit and the at least one imaging unit are both connected to the at least one catheter. The at least one delivery unit, having a longitudinal axis, is configured to deploy a device. The at least one imaging unit has a steerable distal end portion that is selectively moveable between a first position and a second position. In the first position, the imaging unit is generally aligned with the axis of the at least one delivery unit; and in the second position, the imaging unit extends radially outward at an angle relative to the axis of the at least one delivery unit.

Embodiment 2. The integrated imaging and device deployment platform in embodiment 1, wherein the at least one imaging unit comprises at least one embedded sensor configured to provide location information.

Embodiment 3. The integrated imaging and device deployment platform in any of embodiments 1-2, wherein the at least one imaging unit is a mapping catheter.

Embodiment 4. The integrated imaging and device deployment platform in embodiment 3, wherein the mapping catheter is an intra-cardiac echocardiography imaging device.

Embodiment 5. The integrated imaging and device deployment platform in any of embodiments 1-4, wherein the device is a therapeutic device suitable for a medical procedure including surgery or a minimally invasive procedure.

Embodiment 6. The integrated imaging and device deployment platform in embodiment 5, wherein the therapeutic device is a mitral valve or tricuspid valve fixation device.

Embodiment 7. The integrated imaging and device deployment platform in embodiment 5, wherein the therapeutic device is a left atrial appendage (LAA) occluder device.

Embodiment 8. The integrated imaging and device deployment platform in any of embodiments 1-7, wherein at least one imaging unit produces imaging information configured to be combined with at least one second imaging modality.

Embodiment 9. The integrated imaging and device deployment platform in embodiment 8, wherein the at least one second imaging modality includes a pre-acquired computed tomography image, a 3D rendering is obtained from a mapping catheter, or a combination thereof.

Embodiment 10. The integrated imaging and device deployment platform in any of embodiments 1-9, wherein the at least one imaging unit is axially movable relative to the at least one delivery unit.

Embodiment 11. The integrated imaging and device deployment platform in any embodiments 1-10, wherein the at least one imaging unit is radially movable and/or rotatable relative to the at least one delivery unit.

Embodiment 12. The integrated imaging and device deployment platform in any of embodiments 1-11 further comprises at least one pull wire connected to the at least one catheter that is connected to the at least one imaging unit and configured to move the at least one imaging unit axially as the at least one pull wire is pulled proximally.

Embodiment 13. The integrated imaging and device deployment platform in any of embodiments 1-12, wherein information from the at least one imaging unit is provided to and displayed on a user interface.

Embodiment 14. The integrated imaging and device deployment platform in any of embodiments 1-13, wherein the at least one catheter includes a first catheter, the at least one delivery unit comprises a second catheter that extends distal to and generally continuously with the first catheter.

Embodiment 15. The integrated imaging and device deployment platform in any of embodiments 1-14, wherein the at least one delivery unit is supported at a distal end of a catheter among the at least one catheter that extends distally and generally continuous with the delivery unit.

Embodiment 16. The integrated imaging and device deployment platform in any of embodiments 1-15 further comprises a connecting portion connecting the at least one imaging unit and the at least one delivery unit to the at least one catheter.

Embodiment 17. A method for deploying a device comprises providing an integrated imaging and device deployment platform comprising at least one catheter, at least one imaging unit connected to the at least one catheter, and at least one delivery unit connected to the at least one catheter. The method further includes navigating the platform to a desired location and utilizing an imaging unit to ascertain a desired configuration and/or location of the platform, and deploying a device from a delivery unit.

Embodiment 18. A method in embodiment 17 further comprises providing a pre-acquired imaging model or rendering the pre-acquired imaging model on a user interface.

Embodiment 19. A method in any of embodiments 17-18, wherein utilizing an imaging unit to ascertain a desired configuration and/or location of the platform further comprises providing real-time imaging information from the at least one imaging unit on a user interface.

Embodiment 20. A method in any of embodiments 17-19 further comprises adjusting a configuration of the platform by moving the at least one imaging unit axially and/or radially relative to the at least one delivery unit.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

It will be understood that, unless a term is defined in this patent to possess a described meaning, there is no intent to limit the meaning of such term, either expressly or indirectly, beyond its plain or ordinary meaning.

It is to be understood that not necessarily all objects or advantages may be achieved under any embodiment of the disclosure. Those skilled in the art will recognize that the method, system, and device for deploying an implant may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to make or use a method, system, or device for deploying an implant under principles of the present disclosure. It will be understood by the skilled artisan that the features described may be adapted to other types of devices and processes. Hence this disclosure and the embodiments and variations thereof are not limited to integrated imaging and device deployment platforms and methods, but can be utilized in any suitable process or device and may be utilized for any suitable procedure, including standard surgical procedures.

Although this disclosure describes certain exemplary embodiments and examples of an integrated imaging and device deployment platform and method, it, therefore, will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above.

We claim:

1. An integrated imaging and device deployment platform comprising:
   at least one catheter;
   at least one delivery unit connected to the at least one catheter, the at least one delivery unit having a longitudinal axis and being configured to deploy a device, wherein the at least one delivery unit comprises a catheter and a tether that is detachably coupled to a portion of the device, wherein the catheter of the at least one delivery unit extends coaxially with the at least one catheter; and
   at least one imaging unit connected to the at least one catheter, the at least one imaging unit having a steerable distal end portion that is selectively moveable between a first position in which the imaging unit is generally aligned with the axis of the at least one delivery unit and a second position in which the imaging unit extends radially outward at an angle relative to the axis of the at least one delivery unit, wherein, in the second position the delivery unit extends through one portion of a connecting portion and the imaging unit extends through another portion of the connecting portion.

2. The integrated imaging and device deployment platform of claim 1, wherein the at least one imaging unit comprises at least one embedded sensor configured to provide location information.

3. The integrated imaging and device deployment platform of claim 1, wherein the at least one imaging unit is a mapping catheter.

4. The integrated imaging and device deployment platform of claim 3, wherein the mapping catheter is an intracardiac echocardiography imaging device.

5. The integrated imaging and device deployment platform of claim 1, wherein the device is a therapeutic device suitable for a medical procedure including surgery or a minimally invasive procedure.

6. The integrated imaging and device deployment platform of claim 5, wherein the therapeutic device is a mitral valve or tricuspid valve fixation or similar valve repair device.

7. The integrated imaging and device deployment platform of claim 5, wherein the therapeutic device is a left atrial appendage (LAA) occluder.

8. The integrated imaging and device deployment platform of claim 1, wherein the at least one imaging unit produces imaging information configured to be combined with imaging information produced by at least one second imaging modality.

9. The integrated imaging and device deployment platform of claim 8, wherein the at least one second imaging modality includes a pre-acquired computed tomography image, a three-dimensional (3D) rendering obtained from a mapping catheter, or a combination thereof.

10. The integrated imaging and device deployment platform of claim 1, wherein the at least one imaging unit is axially movable relative to the at least one delivery unit.

11. The integrated imaging and device deployment platform of claim 1, wherein the at least one imaging unit is radially movable relative to the at least one delivery unit.

12. The integrated imaging and device deployment platform of claim 10, further comprising at least one pull wire connected to the at least one catheter that is connected to the at least one imaging unit and configured to move the at least one imaging unit axially as the at least one pull wire is pulled proximally.

13. The integrated imaging and device deployment platform of claim 1, wherein information from the at least one imaging unit is provided to and displayed on a user interface.

14. The integrated imaging and device deployment platform of claim 1, wherein the at least one catheter includes a first catheter, the at least one delivery unit comprises a second catheter that extends distal to and generally continuously with the first catheter.

15. The integrated imaging and device deployment platform of claim 1, wherein the at least one imaging unit is supported at a distal end of a catheter among the at least one catheter that extends distally and generally continues with the delivery unit.

16. The integrated imaging and device deployment platform of claim 1, further comprising a connecting portion connecting the at least one imaging unit and the at least one delivery unit to the at least one catheter.

17. A method for deploying a device, comprising:
   providing an integrated imaging and device deployment platform comprising at least one catheter, at least one imaging unit connected to the at least one catheter, and at least one delivery unit connected to the at least one catheter, wherein the delivery unit comprises a catheter and a tether that is detachably coupled to a portion of a device to be deployed and the deployment platform is configured to be in a first position or a second position, wherein the first position includes the imaging unit generally aligned with the axis of the at least one delivery unit and the second position includes the imaging unit extending radially outward at an angle relative to the axis of the at least one delivery unit, wherein in the second position the delivery unit goes through one portion of a connecting portion and the imaging unit goes through another portion of the connecting portion;

navigating the platform to a desired location;

utilizing an imaging unit to ascertain a desired configuration and/or location of the platform;

adjusting the at least one imaging unit relative to a delivery unit in each of three degrees of movement, wherein the three degrees of movement comprise rotating about a main axis of the at least one catheter, tilting and angling the at least one imaging unit; and deploying the device from the delivery unit.

18. The method of claim 17, further comprising:

providing a pre-acquired imaging model or rendering the pre-acquired imaging model on a user interface.

19. The method of claim 17, wherein utilizing an imaging unit to ascertain a desired configuration and/or location of the platform further comprises:

providing real-time imaging information from the at least one imaging unit on a user interface.

20. The method of claim 17, further comprising:

adjusting a configuration of the platform by moving the at least one imaging unit axially and/or radially relative to the at least one delivery unit.

\* \* \* \* \*